US008828929B2

(12) United States Patent
Matsui et al.

(10) Patent No.: US 8,828,929 B2
(45) Date of Patent: Sep. 9, 2014

(54) CYTOTOXIC T CELL EPITOPE PEPTIDE FOR SARS CORONAVIRUS, AND USE THEREOF

(75) Inventors: Masanori Matsui, Saitama (JP); Tetsuya Uchida, Tokyo (JP); Hiroshi Oda, Kawasaki (JP)

(73) Assignees: Nof Corporation, Tokyo (JP); Saitama Medical University, Saitama (JP); Japan as Represented by Director-General of National Institute of Infectious Diseases, Tokyo (JP)

( * ) Notice: Subject to any disclaimer, the term of this patent is extended or adjusted under 35 U.S.C. 154(b) by 0 days.

(21) Appl. No.: 13/131,560

(22) PCT Filed: Nov. 27, 2009

(86) PCT No.: PCT/JP2009/070043
§ 371 (c)(1),
(2), (4) Date: Jul. 7, 2011

(87) PCT Pub. No.: WO2010/061919
PCT Pub. Date: Jun. 3, 2010

(65) Prior Publication Data
US 2011/0262529 A1 Oct. 27, 2011

(30) Foreign Application Priority Data
Nov. 28, 2008 (JP) .............................. P2008-304965

(51) Int. Cl.
*A61K 39/12* (2006.01)
*A61K 38/08* (2006.01)
*A61K 9/127* (2006.01)
*C07K 7/06* (2006.01)
*A61P 31/12* (2006.01)
*A61K 39/215* (2006.01)
*C07K 14/005* (2006.01)
*A61K 39/00* (2006.01)

(52) U.S. Cl.
CPC ....... *A61K 9/127* (2013.01); *C12N 2770/20034* (2013.01); *A61K 2039/60* (2013.01); *A61K 39/215* (2013.01); *A61K 2039/55555* (2013.01); *C07K 14/005* (2013.01); *C12N 2770/20022* (2013.01)
USPC ......... 514/3.7; 424/450; 424/186.1; 530/328; 514/21.6

(58) Field of Classification Search
CPC ..... A61K 9/127; A61K 39/215; A61K 38/08; A61K 2039/55555; A61K 2039/60; C07K 14/005; C12N 2770/20022; C12N 2770/20034
See application file for complete search history.

(56) References Cited

U.S. PATENT DOCUMENTS

| 7,897,744 B2 | 3/2011 | Plummer et al. | |
| 2008/0038329 A1* | 2/2008 | Uchida et al. | 424/450 |
| 2010/0136098 A1* | 6/2010 | Uchida et al. | 424/450 |

FOREIGN PATENT DOCUMENTS

| CN | 1483737 A | * | 3/2004 | ........... C07K 14/165 |
| CN | 1572875 A | | 2/2005 | |
| WO | 00/23053 A2 | | 4/2000 | |
| WO | WO 2004092360 A2 | * | 10/2004 | |
| WO | 2004/096842 A2 | | 11/2004 | |
| WO | 2004/110349 A2 | | 12/2004 | |

OTHER PUBLICATIONS

Definition of prophylaxis, from http://dictionary.reference.com/browse/prophylaxis, pp. 1-3. Accessed Aug. 9, 2012.*
Weiss et al., Coronavirus Pathogenesis and the Emerging Pathogen Severe Acute Respiratory Syndrome Coronavirus, Microbiol. Mol. Biol. Rev., 2005, 69, pp. 635-664.*
Marra et al., The Genome Sequence of the SARS-Associated Coronavirus, Science, 2003, 300, pp. 1399-1404.*
Rota et al., Characterization of a Novel Coronavirus Associated with Severe Acute Respiratory Syndrome, Science, 2003, 300, pp. 1394-1399.*
Stockman et al., SARS: Systematic Review of Treatment Effects, PLoS Med., 2006, 3(9), pp. 1525-1531.*
Cavanagh, Severe acute respiratory syndrome vaccine development: experiences of vaccination against avian infectious bronchitis coronavirus, Avian Pathol., 2003, 32(6), pp. 567-582.*
Kohyama et al., Efficient induction of cytotoxic T lymphocytes specific for severe acute respiratory syndrome (SARS)-associated coronavirus by immunization with surface-linked liposomal peptides derived from a non-structural polyprotein 1a, Antiviral Research, 2009, 84, pp. 168-177.*
Schirle et al, Combining computer algorithms with experimental approaches permits the rapid and accurate identification of T cell epitopes from defined antigens, Journal of Immunological Methods, 2001, 257, pp. 1-16.*
Machine translation of CN 1483737 A, pp. 1-46, publication date Mar. 24, 2004.*
Japanese Patent Office as International Searching Authority, International Preliminary Report on Patentability issued Jul. 14, 2011 in International Application No. PCT/JP2009/070043.
Thomas G. Ksiazek, et al., "A Novel Coronavirus Associated with Severe Acute Respiratory Syndrome", The New England Journal of Medicine, May 15, 2003, pp. 1953-1966, vol. 348, No. 20.

(Continued)

Primary Examiner — Julie Ha
Assistant Examiner — Li Ni Komatsu
(74) Attorney, Agent, or Firm — Sughrue Mion, PLLC

(57) ABSTRACT

The present invention aims to provide a novel CTL epitope peptide of the SARS coronavirus. The present invention provides a peptide having an amino acid sequence selected from the group consisting of SEQ ID NOs: 10, 11, 12, 13, 15, 17, 18, 23 and 24.

14 Claims, 3 Drawing Sheets

(56) References Cited

OTHER PUBLICATIONS

Marco A. Marra, et al., "The Genome Sequence of the SARS-Associated Coronavirus", Science, May 1, 2003, pp. 1399-1404, vol. 300(5624).

Zhi-Yong Yang, et al., "A DNA Vaccine Induces SARS Coronavirus Neutralization and Protective Immunity in Mice", Letter to Nature, Apr. 1, 2004, pp. 561-564, vol. 428 (6982).

Yue-Dan Wang, et al., "T-Cell Epitopes in Severe Acute Respiratory Syndrome (SARS) Coronavirus Spike Protein Elicit a Specific T-Cell Immune Response in Patients Who Recover from SARS", Journal of Virology, Jun. 2004, pp. 5612-5618, vol. 78, No. 11.

Huabiao Chen, et al., "Response of Memory CD8+ T Cells to Severe Acute Respiratory Syndrome (SARS) Coronavirus in Recovered SARS Patients and Healthy Individuals", Journal of Immunology, Jul. 1, 2005, pp. 591-598, vol. 175 (1).

Minghai Zhou, et al., "Screening and Identification of Severe Acute Respiratory Syndrome-Associated Coronavirus-Specific CTL Epitopes", Journal of Immunology, Aug. 15, 2006, pp. 2138-2145, vol. 177 (4).

Maiko Taneichi, et al., "Antigen Chemically Coupled to the Surface of Liposomes Are Cross-Presented to CD8+ T Cells and Induce Potent Antitumor Immunity", Journal of Immunology, 2006, pp. 2324-2330, vol. 177.

Tomoya Nagata, et al., "Peptides Coupled to the Surface of a Kind of Liposome Protect Infection of Influenza Viruses", Vaccine, 2007, pp. 4914-4921, vol. 25.

Xiaofen Zhong, et al., "B-Cell Responses in Patients Who Have Recovered from Severe Acute Respiratory Syndrome Target a Dominant Site in the S2 Domain of the Surface Spike Glycoprotein", Journal of Virology, Mar. 2005, pp. 3401-3408, vol. 79. No. 6.

Chris Ka-Fai Li, et al., "T Cell Response to Whole SARS Coronavirus in Humans", Journal of Immunology, 2008, pp. 5490-5500, vol. 181.

WIPO, International Search Report for PCT/JP2009/070043 dated Dec. 28, 2009.

Chinese Patent Office, Chinese Office Action issued in corresponding CN Application No. 200980147596.5, dated Dec. 31, 2012.

Berry et al., "Development and Characterisation of Neutralising Monoclonal Antibody to the SARS-coronavirus," Journal of Virological Methods, 2004, vol. 120, pp. 87-96.

Rao et al., "Cytotoxic T Lymphocytes to Ebola Zaire Virus are Induced in Mice by Immunization with Lipsomes Containing Lipid A," Vaccine, 1999, vol. 19, No. 23-24, pp. 2991-2998.

European Patent Office, European Search Report issued in corresponding EP Application No. 09829164.4, dated Feb. 20, 2013.

* cited by examiner

CYTOTOXIC T CELL EPITOPE PEPTIDE FOR SARS CORONAVIRUS, AND USE THEREOF

CROSS REFERENCE TO RELATED APPLICATIONS

This application is a National Stage of International Application No. PCT/JP2009/070043 filed Nov. 27, 2009, claiming priority based on Japanese Patent Application No. 2008-304965, filed Nov. 28, 2008, the contents of all of which are incorporated herein by reference in their entirety.

TECHNICAL FIELD

The present invention relates to a cytotoxic T cell epitope peptide for the SARS coronavirus and use thereof.

BACKGROUND ART

Severe Acute Respiratory Syndrome (SARS) is an emerging infectious disease with a high lethality caused by the novel SARS coronavirus (SARS-CoV). Since the outbreak of the disease in 2003 in China, not less than 8000 people have been infected and about 800 people have died. However, no effective prophylactic or therapeutic method for the disease exists so far. After the outbreak of SARS, the SARS virus, which is the causative virus of SARS, was identified (Non-patent Document 1), and its base sequence has been determined (Non-patent Document 2).

The SARS coronavirus is a novel species of coronavirus belonging to Coronaviridae, a group of single-stranded (+) RNA viruses. The genome size of the SARS coronavirus is 29.7 kb, which is very large (Non-patent Document 2), and the genome encodes 23 putative proteins. As major structural proteins, there are Spike (1256 aa), Nucleocapsid (423 aa), Membrane (222 aa) and Small Envelope (77 aa). As nonstructural proteins, there are two polyproteins pp1a (4382 aa, SEQ ID NO:31; GenBank Accession No. AAP13439) and pp1b (2696 aa), and from these polyproteins, individual proteins are cleaved out by proteases in a site-specific manner.

CITATION LIST

Non Patent Literature

Non-patent Document 1: Ksiazek, T. G. et al., N. Engl. J. Med. 348:1953-1966 (2003)
Non-patent Document 2: Marra, M. A. et al., Science 300: 1399-1404 (2003)
Non-patent Document 3: Yang, Z. Y. et al., Nature 428:561-564 (2004)
Non-patent Document 4: Wang. Y. D. et al., J. Virol. 78:5612-5618 (2004)
Non-patent Document 5: Chen, H. et al., J. Immunol. 175: 591-598 (2005)
Non-patent Document 6: Zhou, M. et al., J. Immunol. 177: 2138-2145 (2006)

SUMMARY OF INVENTION

Technical Problem

It has been reported so far that a virus-neutralizing antibody is induced by a DNA vaccine encoding the Spike protein (Non-patent Document 3). Although humoral immunity and cell-mediated immunity are necessary for effective defense reaction, cell-mediated immunity has been less studied compared to humoral immunity in the field of the SARS coronavirus. Cytotoxic T lymphocytes (CTLs) play an important role for protection against viruses in cell-mediated immunity, and therefore a new therapeutic method may be provided by controlling the CTL activity specific to the SARS coronavirus. From this viewpoint, identification of a strong CTL epitope peptide having a high antigenicity among the SARS coronavirus proteins has been demanded. Several types of partial peptides derived from the Spike protein, which is a structural protein, have been identified so far as CTL epitope peptides specific to the SARS coronavirus (Non-patent Documents 4 to 6). However, CTL epitope peptides derived from nonstructural proteins have not been reported yet.

The present invention aims to provide a novel CTL epitope peptide of the SARS coronavirus. More particularly, the present invention aims to provide a peptide comprising a novel CTL epitope derived from the SARS coronavirus pp1a protein, a peptide-bound liposome and an antigen presenting cell. Furthermore, the present invention aims to provide an inducing agent for HLA-A2-restricted CTLs, which comprises the peptide, the peptide-bound liposome or the antigen presenting cell as an active ingredient and is specific to the SARS coronavirus. The present invention also aims to provide a vaccine and the like for therapy or prophylaxis of infection by the SARS coronavirus.

Solution to Problem

The present inventors carried out the following studies in order to identify a CTL epitope derived from the SARS coronavirus, which has not been reported so far. First, by focusing on the pp1a protein, which is a nonstructural protein of the SARS coronavirus, 30 kinds of peptides were selected among peptides predicted as candidates of the epitope. Subsequently, the binding affinity to the HLA-A2 molecule, which is a MHC class I molecule, was confirmed for the peptides, and 9 kinds of peptides among the epitope candidate peptides were found to have significant CTL inducing activities. Furthermore, it was revealed that, by immunization with peptide-bound liposomes containing the peptides, the CTL induction is initiated and the CTL response is activated in vivo. Based on these findings, the present inventors succeeded in providing peptides comprising novel CTL epitopes derived from the SARS coronavirus pp1a protein, thereby completing the present invention.

That is, the present invention provides a peptide comprising an amino acid sequence selected from the group consisting of SEQ ID NOs: 10, 11, 12, 13, 15, 17, 18, 23 and 24. Furthermore, the peptide of the present invention preferably comprises an amino acid sequence selected from the group consisting of SEQ ID NOs: 10, 12, 15, 17 and 24, and more preferably comprises the amino acid sequence shown in SEQ ID NO:24. The peptide of the present invention is characterized in that it comprises a cytotoxic T cell epitope specific to the SARS coronavirus, and that it comprises an HLA-A2-restricted cytotoxic T cell epitope.

The present invention provides a peptide-bound liposome, wherein a peptide is bound to the surface of a liposome, wherein the liposome comprises a phospholipid comprising a $C_{14}$-$C_{24}$ acyl group containing one unsaturated bond, or a $C_{14}$-$C_{24}$ hydrocarbon group containing one unsaturated bond, and a stabilizer, and wherein the peptide is at least one peptide selected from the above-described peptide.

The above-described phospholipid preferably comprises a $C_{14}$-$C_{24}$ acyl group containing one unsaturated bond, and more preferably comprising an oleoyl group. Furthermore, the above phospholipid is preferably at least one selected from the group consisting of diacylphosphatidylserine, diacylphosphatidylglycerol, diacylphosphatidic acid, diacylphosphatidylcholine, diacylphosphatidylethanolamine, succinimidyl-diacylphosphatidylethanolamine and maleimide-diacylphosphatidylethanolamine.

If the phospholipid comprised in the liposome has such a constitution, CTLs for killing pathogen-infected cells can be efficiently enhanced, and prophylaxis and therapy of infectious diseases becomes possible.

The above-described stabilizer is preferably a cholesterol. By this constitution, the above liposome can be more stabilized.

The above-described peptide is preferably bound to the phospholipid comprised in the liposome. By this way, the peptide can be presented on the surface of the liposome, thereby CTLs specific to the SARS coronavirus can be induced more effectively.

Furthermore, the peptide-bound liposome of the present invention preferably comprises the following constituents:

(A) 1 to 99.8 mol % of a phospholipid comprising a $C_{14}$-$C_{24}$ acyl group containing one unsaturated bond, or a $C_{14}$-$C_{24}$ hydrocarbon group containing one unsaturated bond; and (B) 0.2 to 75 mol % of a stabilizer.

Furthermore, the peptide-bound liposome of the present invention preferably comprises the following constituents:

(I) 1 to 85 mol % of an acidic phospholipid comprising a $C_{14}$-$C_{24}$ acyl group containing one unsaturated bond, or a $C_{14}$-$C_{24}$ hydrocarbon group containing one unsaturated bond;

(II) 0.01 to 80 mol % of a neutral phospholipid comprising a $C_{14}$-$C_{24}$ acyl group containing one unsaturated bond, or a $C_{14}$-$C_{24}$ hydrocarbon group containing one unsaturated bond, at a concentration of;

(III) 0.2 to 80 mol % of a phospholipid comprising a $C_{14}$-$C_{24}$ acyl group containing one unsaturated bond, or a $C_{14}$-$C_{24}$ hydrocarbon group containing one unsaturated bond, wherein the phospholipid is bound to at least one peptide selected from the above-described peptide; and (IV) 0.2 to 75 mol % of a stabilizer.

The present invention provides an antigen presenting cell prepared by contacting a cell expressing a cell surface antigen HLA-A2 with at least one peptide selected from the above-described peptide in vitro. The cell is preferably autologous, and more preferably allogenic.

Furthermore, the present invention provides an inducing agent for HLA-A2-restricted CTLs specific to the SARS coronavirus comprising at least one peptide selected from the above-described peptide, the peptide-bound liposome or the antigen presenting cell as an active ingredient.

The present invention provides a vaccine for prophylaxis of infection by the SARS coronavirus comprising at least one peptide selected from the above-described peptide, the peptide-bound liposome or the antigen presenting cell as an active ingredient.

Furthermore, the present invention provides a method for providing immunity to a subject who needs to be given immunity against the SARS coronavirus comprising administering at least one peptide selected from the above-described peptide, the peptide-bound liposome or the antigen presenting cell to the subject.

The present invention provides a method for providing immunity to a subject who needs to be given immunity against the SARS coronavirus comprising: collecting cells from the subject; preparing antigen presenting cells by contacting the cells with at least one peptide selected from the above-described peptide in vitro; and reinjecting the antigen presenting cells to the subject. The cells are preferably lymphoid monocytes, and more preferably dendritic cells.

Advantageous Effects of Invention

The present invention provides a peptide comprising a novel CTL epitope derived from the SARS coronavirus pp1a protein, a peptide-bound liposome and an antigen presenting cell. Since the CTL induction is initiated and the CTL response is activated in vivo by the peptide, the peptide-bound liposome or the antigen presenting cell, any of the peptide, the peptide-bound liposome and the antigen presenting cell of the present invention can be used as a CTL inducing agent and/or a vaccine for elimination of the SARS coronavirus. Furthermore, since nonstructural proteins are synthesized earlier than structural proteins during the process of virus infection, a virus elimination effect at the initial stage of virus infection can be expected by activating the immune reaction using a CTL epitope derived from the pp1a protein, which is a nonstructural protein.

BRIEF DESCRIPTION OF DRAWINGS

In FIG. 1, the legends "No pep" and "with pep" each indicate that the immunization was conducted using a liposome alone and a peptide-bound liposome, respectively. In FIG. 1, the legends "Lip-pp1a-xxxx" each indicate a peptide-bound liposome wherein the peptide is a SARS coronavirus pp1a epitope having a sequence shown in Table 1.

In FIG. 2, the legends "No pep" and "with pep" each indicate that the immunization was conducted using a liposome alone and a peptide-bound liposome, respectively. In FIG. 2, the legend "Lip-SARS Spike 1203" indicates a peptide-bound liposome wherein the peptide is a SARS Spike 1203 epitope of SEQ ID NO: 34 (FIAGLIAIV).

In FIG. 3, the legends "No pep" and "with pep" each indicate that the immunization was conducted using a liposome alone and a peptide-bound liposome, respectively. In FIG. 3, the legends "Lip-pp1a-xxxx" each indicate a peptide-bound liposome wherein the peptide is a SARS coronavirus pp1a epitope having a sequence shown in Table 1.

DESCRIPTION OF EMBODIMENTS

Figure 1:
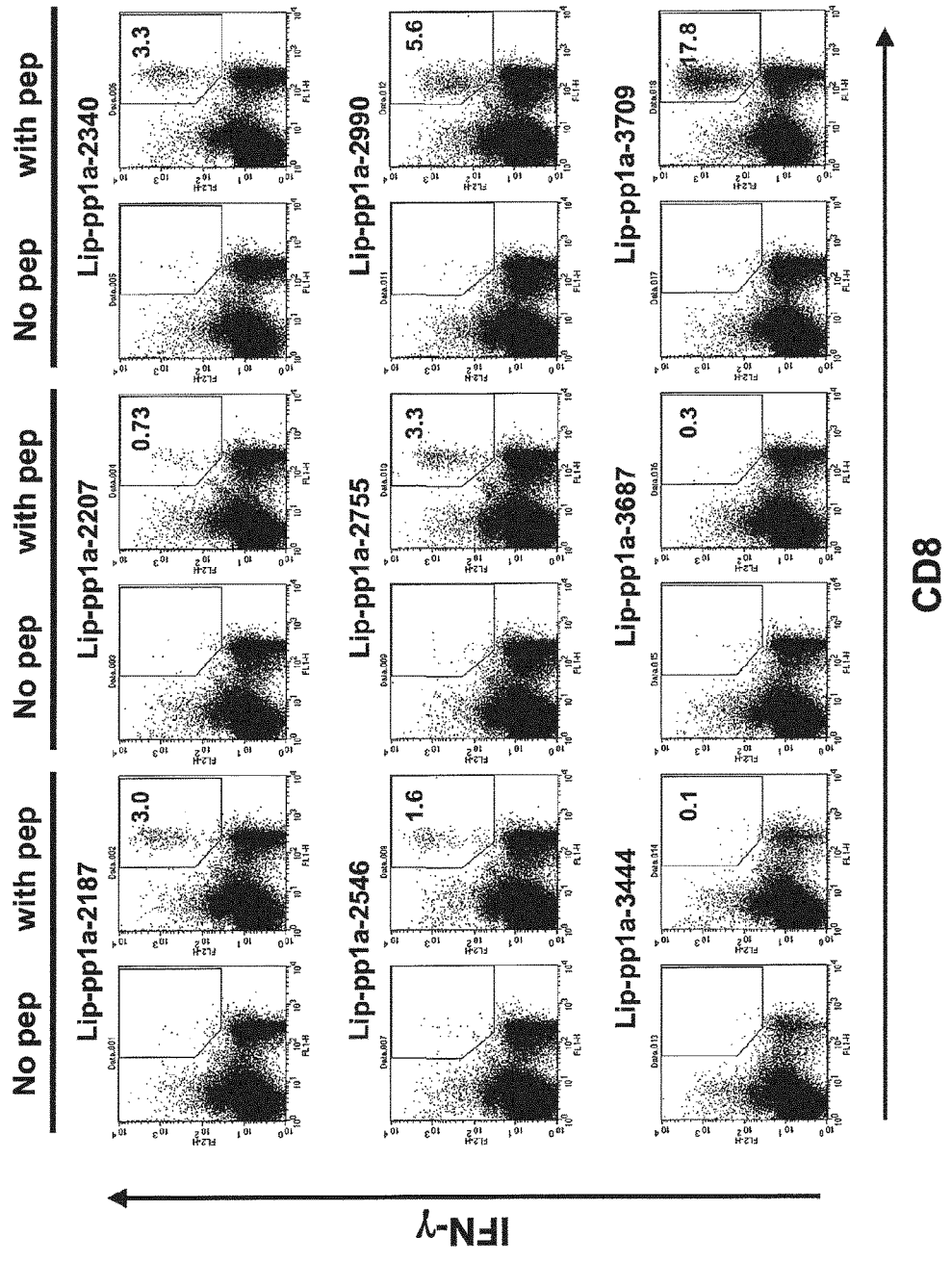
FIG. 1 shows staining plots for CD8 and IFN-γ by flow cytometry in mice immunized with a peptide-bound liposome.
Figure 2:
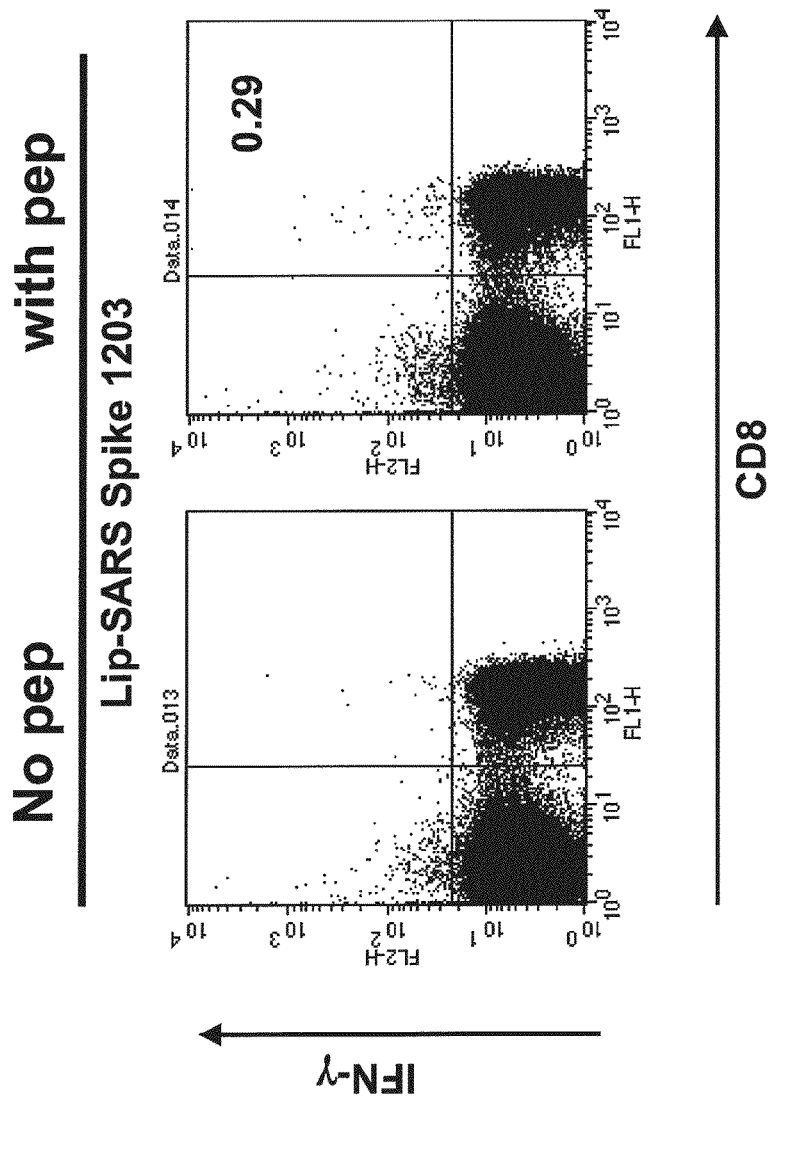
FIG. 2 shows staining plots for CD8 and IFN-γ by flow cytometry in mice immunized with a spike-1203-peptide-bound liposome.
Figure 3:
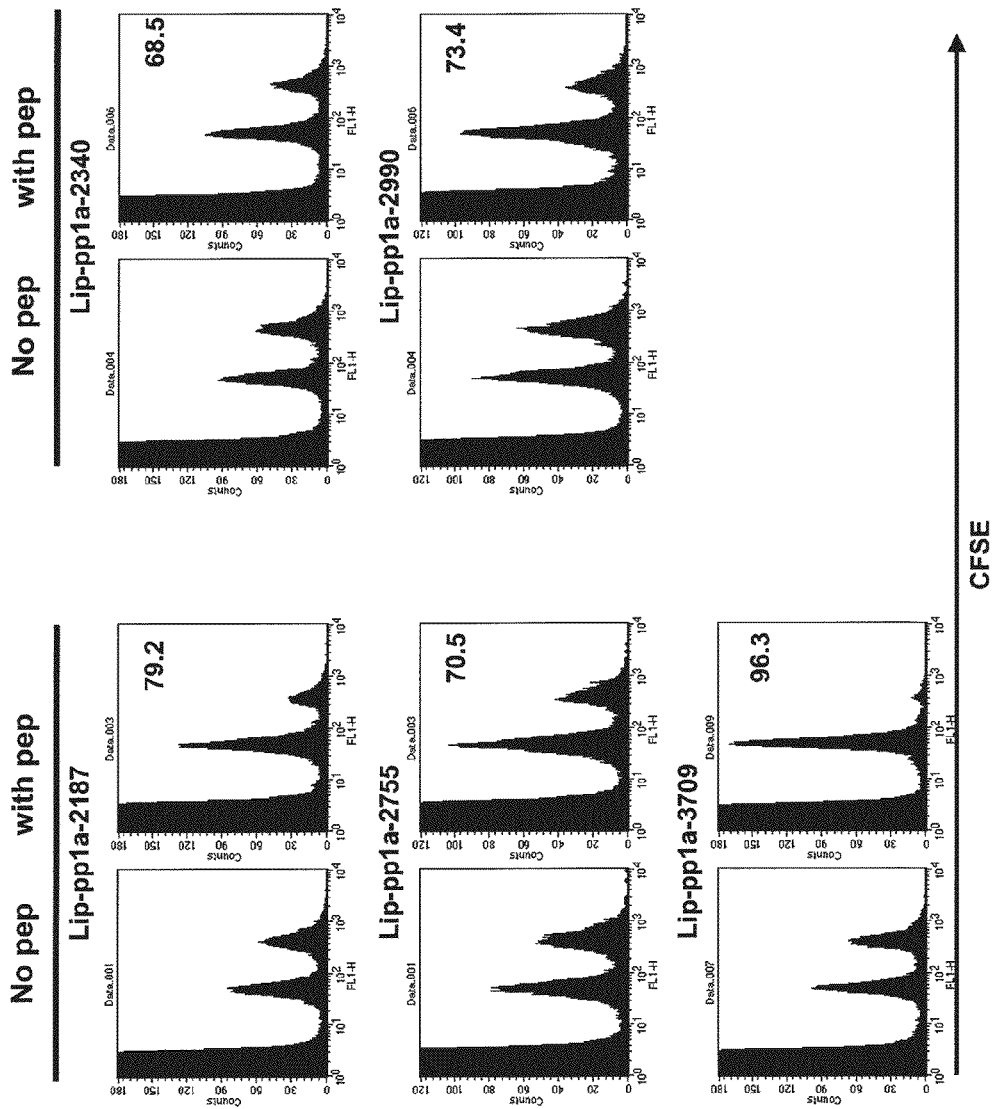
FIG. 3 shows staining plots for CFSE (carboxy fluorescein diacetate succinimidyl ester) by flow cytometry in mice which were booster-immunized with CFSE-labeled antigen presenting cells.

The best mode for carrying out the invention will be described in detail below.

The peptide in the present invention comprises a CTL epitope derived from the SARS coronavirus pp1a protein, and particular examples thereof include peptides containing an amino acid sequence selected from the group consisting of SEQ ID NOs: 10, 11, 12, 13, 15, 17, 18, 23 and 24, and peptides comprising an amino acid sequence selected from the group consisting of SEQ ID NOs: 10, 11, 12, 13, 15, 17, 18, 23 and 24. Furthermore, an amino acid sequence selected from the group consisting of SEQ ID NOs: 10, 12, 15, 17 and 24 is preferred, and the amino acid sequence shown in SEQ ID NO:24 is more preferred. These peptides comprise an HLA-A2-restricted CTL epitope, more particularly, an HLA-A*0201-restricted CTL epitope. The peptide of the present invention may be used in various forms (e.g., unmodified, fusion, glycosylated and nonglycosylated), and may contain a C-terminal modification (amidation, esterification, modification with aldehyde or the like), N-terminal modification (acetylation, biotinylation, fluorescent labeling or the like) and chemical modification of a functional group (phosphorylation, sulfation, biotinylation or the like).

The peptide may be synthesized according to a method used in conventional peptide chemistry. Examples of the known method of peptide synthesis include those described in literatures (Peptide Synthesis, Interscience, New York, 1966; The Proteins, Vol 2, Academic Press Inc., New York, 1976; Peptide Synthesis, MARUZEN Co., Ltd., 1975; Fundamentals and Experiments of Peptide Synthesis, MARUZEN Co., Ltd., 1985; Development of Pharmaceuticals, Continued Edition, Vol. 14, Peptide Synthesis, Hirokawa Shoten, 1991) and the like.

The peptide of the present invention as described above may be used solely or in combination of plural types of peptides as an inducing agent for HLA-A2-restricted CTLs specific to the SARS coronavirus and/or as a vaccine for therapy or prophylaxis of infection of the SARS coronavirus. That is, since the peptide of the present invention can bind to a HLA-A2 molecule and is presented by cells that express the HLA-A2 molecule, thereby strongly induce CTLs, the peptide of the present invention can be used as a CTL inducing agent and/or a vaccine for elimination of the SARS coronavirus.

The liposome used for the peptide-bound liposome of the present invention is a phospholipid bilayer membrane having a closed space.

The liposome used for the peptide-bound liposome of the present invention comprises: a phospholipid comprising a $C_{14}$-$C_{24}$ acyl group containing one unsaturated bond, or a $C_{14}$-$C_{24}$ hydrocarbon group containing one unsaturated bond; and a stabilizer. A phospholipid comprising a $C_{14}$-$C_{24}$ acyl group containing one unsaturated bond is preferably used as the phospholipid.

The carbon number of the acyl group in the phospholipid comprising a $C_{14}$-$C_{24}$ acyl group containing one unsaturated bond is preferably 16 to 22, more preferably 18 to 22, and most preferably 18. Particular examples of the acyl group include palmitoleoyl, oleoyl and erucoyl, and most preferably oleoyl. The carbon number of the hydrocarbon group in the phospholipid comprising a $C_{14}$-$C_{24}$ hydrocarbon group containing one unsaturated bond is preferably 16 to 22, more preferably 18 to 22, and most preferably 18. Particular examples of the hydrocarbon group include tetradecenyl, hexadecenyl, octadecenyl, $C_{20}$ monoene, $C_{22}$ monoene and $C_{24}$ monoene and the like. The unsaturated acyl groups or unsaturated hydrocarbon groups bound to the 1-position and the 2-position of the glycerin residue comprised in the phospholipid may be either the same or different. In view of industrial productivity, the groups at the 1-position and the 2-position are preferably the same.

In view of enhancement of the CTL activity to a practically sufficient level, the phospholipid preferably comprises a $C_{14}$-$C_{24}$ acyl group containing one unsaturated bond. In cases where the carbon number of the acyl group is less than 13, the liposome may be unstable, or the CTL activity enhancement effect may be insufficient. In cases where the carbon number of the acyl group is more than 24, the liposome may be unstable.

Examples of the phospholipid comprising a $C_{14}$-$C_{24}$ acyl group containing one unsaturated bond, or comprising a $C_{14}$-$C_{24}$ hydrocarbon group containing one unsaturated bond include acidic phospholipids, neutral phospholipids, and reactive phospholipids comprising a functional group to which a peptide can be bound. Their types and ratios may be selected depending on various demands.

Examples of the acidic phospholipids which may be used include phosphatidylserine, phosphatidylglycerol, phosphatidic acid and phosphatidylinositol. In view of enhancement of the CTL activity to a practically sufficient level, industrial supply capacity, quality for use as a pharmaceutical, and the like, diacylphosphatidylserine, diacylphosphatidylglycerol, diacylphosphatidic acid and diacylphosphatidylinositol comprising a $C_{14}$-$C_{24}$ acyl group containing one unsaturated bond are preferably used. Since an acidic phospholipid gives an anionic group on the surface of a liposome, a negative zeta potential is given on the surface of the liposome. Therefore, the liposome gains charge repulsion and can exist as a stable formulation in an aqueous solvent. Thus, an acidic phospholipid is important in view of ensuring the stability of the liposome in an aqueous solvent.

Examples of the neutral phospholipids include phosphatidylcholine. The neutral phospholipids which may be employed in the present invention may be used by selecting their types and amounts appropriately within the ranges in which enhancement of the CTL activity can be achieved. Compared to an acidic phospholipid and a phospholipid to which a peptide is bound, a neutral phospholipid has a higher function to stabilize a liposome and hence can enhance the stability of the membrane. From this viewpoint, the liposome to be used for the peptide-bound liposome of the present invention preferably contains a neutral phospholipid. The amount of the neutral phospholipid to be used can be determined after securing the contents of the acidic phospholipid for achievement of the CTL activity enhancement effect, the reactive phospholipid for the peptide bond and the stabilizer.

The peptide of the present invention is bound to the surface of the liposome by being bound to a phospholipid comprising a $C_{14}$-$C_{24}$ acyl group containing one unsaturated bond, or a $C_{14}$-$C_{24}$ hydrocarbon group containing one unsaturated bond, wherein the phospholipid is comprised in the liposome. As the phospholipid for such binding of the peptide, a reactive phospholipid comprising a functional group to which the peptide can be bound is used. The type and the amount of the reactive phospholipid comprising a $C_{14}$-$C_{24}$ acyl group containing one unsaturated bond, or comprising a $C_{14}$-$C_{24}$ hydrocarbon group containing one unsaturated bond are appropriately selected depending on various demands. Similarly to the case of the above-described phospholipid, it is also not preferred that the carbon number of the unsaturated acyl group or the unsaturated hydrocarbon group comprised in the phospholipid is more than 24 or less than 14 in the case of the reactive phospholipid.

Examples of the reactive phospholipid include phosphatidylethanolamine and terminally modified derivatives thereof. Furthermore, phosphatidylglycerol, phosphatidylserine, phosphatidic acid and phosphatidylinositol, and terminally modified derivatives thereof may also be used as the reactive phospholipid. In view of industrial availability, simplicity of the process of binding with a peptide, yield and the like, phosphatidylethanolamine or a terminally modified derivatives thereof is preferably used. Phosphatidylethanolamine has an amino group to which an antibody can be bound at its terminus. Furthermore, in view of enhancement of the CTL activity to a practically sufficient level, stability in a liposome, industrial supply capacity, quality for use as a pharmaceutical, and the like, diacylphosphatidylethanolamine comprising a $C_{14}$-$C_{24}$ acyl group containing one unsaturated bond or a terminally modified derivatives thereof is most preferably used.

Diacylphosphatidylethanolamine can be obtained by, for example, using diacylphosphatidylcholine as a crude material and carrying out a base-exchange reaction of choline and ethanolamine using phospholipase D. More particularly, a solution of diacylphosphatidylcholine in chloroform is mixed at an appropriate ratio with water in which phospholipase D and ethanolamine are dissolved, to obtain a crude reaction product. The crude reaction product is purified with a silica gel column using a chloroform/methanol/water solvent, thereby obtaining the diacylphosphatidylethanolamine of interest. Those skilled in the art can carry out the purification by appropriately selecting the conditions for purification by the column, such as the composition ratio of the solvent.

Examples of the terminally modified derivatives include a terminally modified diacylphosphatidylethanolamine produced by binding one of the termini of a divalent reactive compound to the amino group of diacylphosphatidylethanolamine. Examples of the divalent reactive compound which may be used include compounds comprising, at least one terminus, an aldehyde group or a succinimide group which can react with the amino group of diacylphosphatidylethanolamine. Examples of the divalent reactive compound comprising an aldehyde group include glyoxal, glutaraldehyde, succindialdehyde and terephthalaldehyde. Preferred examples thereof include glutaraldehyde. Examples of the divalent reactive compound comprising a succinimide group include dithiobis(succinimidylpropionate), ethylene glycolbis(succinimidylsuccinate), disuccinimidyl succinate, disuccinimidyl suberate and disuccinimidyl glutarate.

Furthermore, examples of the divalent reactive compound comprising a succinimide group at one terminus and a maleimide group at the other terminus include N-succinimidyl4-(p-maleimidophenyl)butyrate, sulfosuccinimidyl-4-(p-maleimidophenyl)butyrate, N-succinimidyl-4-(p-maleimidophenyl)acetate, N-succinimidyl-4-(p-maleimidophenyl)propionate, succinimidyl-4-(N-maleimidoethyl)-cyclohexane-1-carboxylate, sulfosuccinimidyl-4-(N-maleimidoethyl)-cyclohexane-1-carboxylate, N-(γ-maleimidobutyryloxy)succinimide and N-(ε-maleimidocaproyloxy)succinimide. By using such a divalent reactive compound, a terminally modified diacylphosphatidylethanolamine comprising a maleimide group as a functional group is obtained. By binding a functional group at one terminus of such a divalent reactive compound to the amino group of diacylphosphatidylethanolamine, a terminally modified diacylphosphatidylethanolamine can be obtained.

Examples of the method for binding the peptide to the surface of the liposome include a method wherein a liposome comprising the above reactive phospholipid is prepared and the peptide is then added thereto to bind the peptide to the reactive phospholipid in the liposome. Furthermore, by preliminarily binding the peptide to the reactive phospholipid and mixing the obtained peptide-bound reactive phospholipid with a phospholipid other than a reactive phospholipid and a stabilizer, a liposome in which the peptide is bound to its surface can also be obtained. The method for binding a peptide to a reactive phospholipid is well-known in the art.

The liposome to be used for the peptide-bound liposome of the present invention comprises at least 1 type, for example, 2 or more types, preferably 3 or more types of phospholipid(s) comprising a $C_{14}$-$C_{24}$ acyl group containing one unsaturated bond, or a $C_{14}$-$C_{24}$ hydrocarbon group containing one unsaturated bond. For example, the liposome to be used in the peptide-bound liposome of the present invention comprises at least 1 type, for example, 2 or more types, preferably 3 or more types of phospholipid(s) comprising a $C_{14}$-$C_{24}$ acyl group containing one unsaturated bond, or a $C_{14}$-$C_{24}$ hydrocarbon group containing one unsaturated bond selected from diacylphosphatidylserine, diacylphosphatidylglycerol, diacylphosphatidic acid, diacylphosphatidylcholine, diacylphosphatidylethanolamine, succinimidyl-diacylphosphatidylethanolamine and maleimide-diacylphosphatidylethanolamine.

Furthermore, the liposome to be used for the peptide-bound liposome of the present invention preferably comprises at least one type of each of:

acidic phospholipid comprising a $C_{14}$-$C_{24}$ acyl group containing one unsaturated bond, or a $C_{14}$-$C_{24}$ hydrocarbon group containing one unsaturated bond;

neutral phospholipid comprising a $C_{14}$-$C_{24}$ acyl group containing one unsaturated bond, or a $C_{14}$-$C_{24}$ hydrocarbon group containing one unsaturated bond; and reactive phospholipid comprising a $C_{14}$-$C_{24}$ acyl group containing one unsaturated bond, or a $C_{14}$-$C_{24}$ hydrocarbon group containing one unsaturated bond.

In the present invention, sterols and tocopherols may be used as the stabilizer of the liposome. The sterols may be those generally known as sterols, and examples thereof include cholesterol, sitosterol, campesterol, stigmasterol and brassicasterol. In view of availability and the like, cholesterol is especially preferably used. The tocopherols may be those generally known as tocopherols, and preferred examples thereof include commercially available α-tocopherol in view of availability and the like.

Furthermore, as long as the effect of the present invention is not adversely affected, the liposome to be used for the peptide-bound liposome of the present invention may contain known liposome constituting components that can constitute a liposome.

Examples of the composition of the liposome to be used for the peptide-bound liposome of the present invention include the following:

(A) 1 to 99.8 mol % of a phospholipid comprising: a $C_{14}$-$C_{24}$ acyl group containing one unsaturated bond, or a $C_{14}$-$C_{24}$ hydrocarbon group containing one unsaturated bond; and (B) 0.2 to 75 mol % of a stabilizer.

The content of each component is represented as mol % with respect to the total constituting components of the peptide-bound liposome.

In view of the stability of the liposome, the content of the component (A) is preferably 10 to 90 mol %, more preferably 30 to 80 mol %, still more preferably 50 to 70 mol %.

In view of the stability of the liposome, the content of the component (B) is preferably 5 to 70 mol %, more preferably 10 to 60 mol %, still more preferably 20 to 50 mol %. In cases where the content of the stabilizer is more than 75 mol %, the stability of the liposome is deteriorated, which is not preferred.

The component (A) comprises the followings:

(a) a phospholipid, to which a peptide is not bound, comprising a $C_{14}$-$C_{24}$ acyl group containing one unsaturated bond, or a $C_{14}$-$C_{24}$ hydrocarbon group containing one unsaturated bond; and (b) a phospholipid, to which a peptide is bound, comprising a $C_{14}$-$C_{24}$ acyl group containing one unsaturated bond, or a $C_{14}$-$C_{24}$ hydrocarbon group containing one unsaturated bond.

The content of the component (a) is usually 0.01 to 85 mol %, preferably 0.1 to 80 mol %, more preferably 0.1 to 60 mol %, still more preferably 0.1 to 50 mol %.

The content of the component (b) is usually 0.2 to 80 mol %, preferably 0.3 to 60 mol %, more preferably 0.4 to 50 mol %, still more preferably 0.5 to 25 mol %. In cases where the content is less than 0.2 mol %, the amount of the peptide becomes low, and therefore it is difficult to activate CTLs to a practically sufficient level. In cases where the content is more than 80 mol %, the stability of the liposome becomes low.

The phospholipid of the component (a) usually includes the above-mentioned acidic phospholipid and neutral phospholipid. The phospholipid of the component (b) includes the above-mentioned reactive phospholipid.

The content of the acidic phospholipid is usually 1 to 85 mol %, preferably 2 to 80 mol %, more preferably 4 to 60 mol %, still more preferably 5 to 40 mol %. In cases where the content is less than 1 mol %, the zeta potential becomes small and the stability of the liposome becomes low, and it is difficult to activate CTLs to a practically sufficient level. On the other hand, in cases where the content is more than 85%, the content of the peptide-bound phospholipid in the liposome becomes low as a result, and therefore it is difficult to activate CTLs to a practically sufficient level.

The content of the neutral phospholipid is usually 0.01 to 80 mol %, preferably 0.1 to 70 mol %, more preferably 0.1 to 60 mol %, still more preferably 0.1 to 50 mol %. In cases where the content is more than 80.0 mol %, the contents of the acidic phospholipid, the peptide-bound phospholipid and the liposome stabilizer comprised in the liposome become low, and it is difficult to activate CTLs to a practically sufficient level.

The peptide-bound phospholipid is obtained by binding a peptide to the reactive phospholipid, and the ratio of binding of the reactive phospholipid to the peptide may be selected within the range in which the effect of the present invention is not adversely affected, by taking the type of the functional group used in the binding, conditions of the binding treatment, and the like into consideration appropriately. For example, in cases where the terminally modified diacylphosphatidylethanolamine obtained by binding one terminus of a divalent reactive compound disuccinimidyl succinate to the terminal amino group of diacylphosphatidylethanolamine is used as the reactive phospholipid, 10 to 99% of the reactive phospholipid can be bound to the peptide depending on selection of various conditions of the binding treatment. In such cases, the reactive phospholipid which is not bound to the peptide is comprised in the liposome as an acidic phospholipid.

Examples of a preferred mode of the peptide-bound liposome of the present invention include the following composition:
(I) 1 to 85 mol % of an acidic phospholipid comprising a $C_{14}$-$C_{24}$ acyl group containing one unsaturated bond, or a $C_{14}$-$C_{24}$ hydrocarbon group containing one unsaturated bond;
(II) 0.01 to 80 mol % of a neutral phospholipid comprising a $C_{14}$-$C_{24}$ acyl group containing one unsaturated bond, or a $C_{14}$-$C_{24}$ hydrocarbon group containing one unsaturated bond;
(III) 0.2 to 80 mol % of a phospholipid, to which at least one peptide selected from the above-described peptide is bound, comprising a $C_{14}$-$C_{24}$ acyl group containing one unsaturated bond, or a $C_{14}$-$C_{24}$ hydrocarbon group containing one unsaturated bond; and
(IV) 0.2 to 75 mol % of a stabilizer.
(100 mol % in total)

Examples of a more preferred mode of the liposome to be used for the peptide-bound liposome of the present invention include the following composition:
the component (I) at a concentration of 2 to 80 mol %;
the component (II) at a concentration of 0.1 to 70 mol %;
the component (III) at a concentration of 0.3 to 60 mol %; and
the component (IV) at a concentration of 10 to 70 mol %.
(100 mol % in total)

Examples of a still more preferred mode of the liposome to be used for the peptide-bound liposome of the present invention include the following composition:
the component (I) at a concentration of 4 to 60 mol %;
the component (II) at a concentration of 0.1 to 60 mol %;
the component (III) at a concentration of 0.4 to 50 mol %; and
the component (IV) at a concentration of 20 to 60 mol %.
(100 mol % in total)

Examples of an especially preferred mode of the liposome to be used for the peptide-bound liposome of the present invention include the following composition:
the component (I) at a concentration of 5 to 40 mol %;
the component (II) at a concentration of 0.1 to 50 mol %;
the component (III) at a concentration of 0.5 to 25 mol %; and
the component (IV) at a concentration of 25 to 55 mol %.
(100 mol % in total)

The carbon number of the unsaturated acyl group or the unsaturated hydrocarbon group to be comprised in the phospholipid in the liposome used in the peptide-bound liposome of the present invention is characteristically 14 to 24, but a phospholipid comprising an unsaturated acyl group or unsaturated hydrocarbon group comprising a carbon number of less than 14 or more than 24 may also be comprised to an extent at which the effect of the present invention is not adversely affected. The ratio of the number of the $C_{14}$-$C_{24}$ unsaturated acyl group or unsaturated hydrocarbon group with respect to the total number of all the unsaturated acyl groups or unsaturated hydrocarbon groups comprised in the phospholipid in the liposome used in the peptide-bound liposome of the present invention is, for example, 50% or more, preferably 60% or more, more preferably 75% or more, still more preferably 90% or more, most preferably 97% or more (for example, substantially 100%).

The liposome to be used for the peptide-bound liposome of the present invention may also comprise a lipid other than a phospholipid, comprising a $C_{14}$-$C_{24}$ acyl group or hydrocarbon group, as long as the effect of the present invention is not adversely affected. The content of the lipid is usually 40 mol % or less, preferably 20 mol % or less, more preferably 10 mol % or less, still more preferably 5 mol % or less (for example, substantially 0 mol %).

The liposome to be used in the present invention can be obtained by, for example, a method wherein a phospholipid as a constituting component, reactive phospholipid, stabilizer, peptide and the like are used and are blended and processed in an appropriate way, followed by adding the resulting product to an appropriate solvent. Examples of the production process include the extrusion method, vortex mixer method, ultrasonic method, surfactant removal method, reverse-phase evaporation method, ethanol injection method, prevesicle method, French press method, W/O/W emulsion method, annealing method and freeze-thaw method. The particle diameter of the liposome is not restricted, however, in view of the stability during storage, the particle diameter is, for example, 20 to 600 nm, preferably 30 to 500 nm, more preferably 40 to 400 nm, still more preferably 50 to 300 nm, most preferably 70 to 230 nm.

In the present invention, in order to enhance the physicochemical stability of the liposome, sugars or polyols may be added to the internal aqueous phase and/or the external aqueous phase during or after preparation of the liposome. In particular, in cases where the liposome needs to be stored for a long time or during formulation, a sugar or a polyol may be added/dissolved as a protective agent for the liposome, followed by removing water by freeze-drying to prepare a lyophilized product of the phospholipid composition.

Examples of the sugars include monosaccharides such as glucose, galactose, mannose, fructose, inositol, ribose and xylose; disaccharides such as saccharose, lactose, cellobiose, trehalose and maltose; trisaccharides such as raffinose and melezitose; oligosaccharides such as cyclodextrin; polysaccharides such as dextrin; and sugar alcohols such as xylitol, sorbitol, mannitol and maltitol. Among these sugars, monosaccharides and disaccharides are preferred, and glucose and saccharose are especially preferred in view of availability and the like.

Examples of the polyols include glycerin compounds such as glycerin, diglycerin, triglycerin, tetraglycerin, pentaglycerin, hexaglycerin, heptaglycerin, octaglycerin, nonaglycerin, decaglycerin and polyglycerin; sugar alcohol compounds such as sorbitol and mannitol; ethylene glycol; diethylene glycol; triethylene glycol; tetraethylene glycol; pentaethylene glycol; hexaethylene glycol; heptaethylene glycol; octaethylene glycol and nonaethylene glycol. Among these, glycerin, diglycerin, triglycerin, sorbitol, mannitol, and polyethylene glycols having molecular weights of 400 to 10,000 are preferred in view of availability. The concentration of the sugars or polyols to be contained in the internal aqueous phase and/or the external aqueous phase is, for example, 1 to 20% by weight, preferably 2 to 10% by weight.

When the peptide-bound liposome of the present invention is produced, the peptide-bound liposome can be simply obtained by preparing a liposome to which the peptide has not been bound yet and then binding the peptide thereto. For example, a liposome which contains a phospholipid, stabilizer and a reactive phospholipid for binding the peptide on the surface of the membrane is prepared as, for example, a liposome liquid, and sucrose, which is one of the sugars, is added to its external aqueous phase to about 2 to 10% by weight and dissolved. This sugar-added formulation is transferred to a 10 ml glass vial and the vial is placed in a shelf freeze dryer, followed by cooling to, for example, $-40°$ C. to freeze the sample, thereby obtaining a lyophilized product by a conventional method. The obtained lyophilized product can be stored for a long time since water has been removed, and, when necessary, by adding a particular peptide and carrying out the following steps, the peptide-bound liposome of the present invention can be simply and rapidly obtained. In cases where the interaction between the peptide and the liposome is strong and strong instability is caused, it is a very simple way to store the liposome at the stage of a lyophilized product like this and to use after binding the peptide when necessary.

The liposome to be used for the peptide-bound liposome of the present invention may comprise a phospholipid to which a peptide is bound. Examples of the method to obtain the liposome containing a phospholipid to which a peptide is bound include the methods by the following (A) and (B).

(A) A liposome containing a phospholipid, a reactive phospholipid and a stabilizer is prepared, and a peptide and a divalent reactive compound are added thereto, followed by linking a functional group of the reactive phospholipid to a functional group of the peptide via the divalent reactive compound. As the divalent reactive compound, the one used for preparation of the terminally modified derivatives of the reactive phospholipid may be similarly used. Particular examples of the divalent reactive compound comprising an aldehyde group include glyoxal, glutaraldehyde, succindialdehyde and terephthalaldehyde. Preferred examples thereof include glutaraldehyde. Examples of the divalent reactive compound comprising a succinimide group include dithiobis(succinimidylpropionate), ethylene glycol-bis(succinimidylsuccinate), disuccinimidyl succinate, disuccinimidyl suberate and disuccinimidyl glutarate. Furthermore, examples of the divalent reactive compound comprising a succinimide group at one terminus and a maleimide group at the other terminus include N-succinimidyl-4-(p-maleimidophenyl)butyrate, sulfosuccinimidyl-4-(p-maleimidophenyl)butyrate, N-succinimidyl-4-(p-maleimidophenyl)acetate, N-succinimidyl-4-(p-maleimidophenyl)propionate, succinimidyl-4-(N-maleimidoethyl)-cyclohexane-1-carboxylate, sulfosuccinimidyl-4-(N-maleimidoethyl)-cyclohexane-1-carboxylate, N-(γ-maleimidobutyryloxy)succinimide and N-(ε-maleimidocaproyloxy)succinimide. By using such a divalent reactive compound, a terminally modified derivatives of a reactive phospholipid comprising a maleimide group as a functional group (e.g., phosphatidylethanolamine) is obtained.

(B) A method wherein a liposome containing a phospholipid, a reactive phospholipid and a stabilizer is prepared, and a peptide is added thereto, followed by linking a functional group of the reactive phospholipid contained in the liposome to a functional group of the peptide, and thereby binding the peptide to the liposome.

Examples of the type of the bond in the above (A) and (B) include an ionic bond, hydrophobic bond and covalent bond, and the type of the bond is preferably a covalent bond. Furthermore, particular examples of the covalent bond include a Schiff base bond, amide bond, thioether bond and ester bond. Both of the above two methods allow binding of the peptide to the reactive phospholipid contained in the liposome, thereby forming a phospholipid to which the peptide is bound in the liposome.

In the method (A), particular examples of the method to bind the liposome as a crude material to the peptide via a divalent reactive compound include a method using a Schiff base bond. Examples of the method to bind the liposome to the peptide via a Schiff base bond include a method wherein a liposome comprising an amino group on its surface is prepared and the peptide is added to a suspension of the liposome, followed by adding dialdehyde as the divalent reactive compound to the resulting mixture and binding the amino group on the surface of the liposome to the amino group in the peptide via a Schiff base.

Particular examples of this binding procedure include the following method.

(A-1) In order to obtain a liposome comprising an amino group on its surface, a reactive phospholipid comprising a $C_{14}$-$C_{24}$ acyl group containing one unsaturated bond, or a $C_{14}$-$C_{24}$ hydrocarbon group containing one unsaturated bond (e.g., phosphatidylethanolamine) is mixed with lipids as crude materials for the liposome (e.g., a phospholipid and a stabilizer for a liposome), to prepare a liposome wherein amino groups exist on the surface of the liposome in a certain amount.

(A-2) A peptide is added to the liposome suspension.

(A-3) Subsequently, glutaraldehyde is added as the divalent reactive compound, and the reaction is allowed to proceed for a certain length of time, thereby allowing a Schiff base bond to be formed between the liposome and the peptide.

(A-4) Thereafter, in order to inactivate the reactivity of the excess glutaraldehyde, glycine as an amino group-containing water-soluble compound is added to the liposome suspension and allowed to react therewith.

(A-5) By a method such as gel filtration, dialysis, ultrafiltration or centrifugation, the peptide unbound to the liposome, the reaction product between glutaraldehyde and glycine, and excess glycine are removed, to obtain a peptide-bound liposome suspension.

Particular examples of the method (B) include a method wherein a reactive phospholipid comprising a functional group that can form an amide bond, thioether bond, Schiff base bond, ester bond or the like is introduced to the phospholipid membrane. Particular examples of such a functional base include succinimide, maleimide, amino, imino, carboxyl, hydroxyl and thiol. Examples of the reactive phospholipid to be introduced to the liposome include the reactive phospholipid comprising a $C_{14}$-$C_{24}$ acyl group containing one unsaturated bond, or a $C_{14}$-$C_{24}$ hydrocarbon group containing one unsaturated bond (e.g., phosphatidylethanolamine) whose amino terminus is modified.

A particular example of the binding procedure will now be described referring to a case in which diacylphosphatidylethanolamine is used.

(B-1) Diacylphosphatidylethanolamine comprising a $C_{14}$-$C_{24}$ acyl group containing one unsaturated bond is reacted with disuccinimidyl succinate by a known method at only one terminus, to obtain disuccinimidyl succinate-bound diacylphosphatidylethanolamine comprising a succinimide group as a functional group at the terminus.

(B-2) The disuccinimidyl succinate-bound diacylphosphatidylethanolamine is mixed with other liposome constituting components (e.g., a phospholipid and a stabilizer) by a known method, to prepare a liposome composition comprising a succinimide group on its surface as a functional group.

(B-3) To the liposome composition suspension, a peptide is added, and the amino group in the peptide is reacted with the succinimide group on the surface of the phospholipid membrane.

(B-4) The unreacted peptides, reaction byproducts and the like are removed by a method such as gel filtration, dialysis, ultrafiltration or centrifugation, to obtain a liposome suspension containing a peptide-bound phospholipid.

In cases where a liposome is bound to a peptide, it is practically preferred to use an amino group or a thiol group, which is often comprised as a functional group. In cases where an amino group is used, a Schiff base bond can be formed by reacting it with a succinimide group. In cases where a thiol group is used, a thioether bond can be formed by reacting it with a maleimide group.

The antigen presenting cell in the present invention is a cell prepared by bringing a cell that expresses the cell surface antigen HLA-A2 into contact with one or more types of peptides in vitro. The cell is preferably autologous and/or allogenic. Examples of the cell include cells that express the cell surface antigen HLA-A2 (e.g., HLA-A*0201). The cell is preferably a lymphoid monocyte (T cell, macrophage, B cell, dendric cell or the like), more preferably a dendritic cell.

The antigen presenting cell of the present invention can be used as an inducer of HLA-A2-restricted CTLs specific to the SARS coronavirus, and/or as a vaccine for therapy or prophylaxis of infection of the SARS coronavirus, by administering (injecting) the cell to a subject. That is, the antigen presenting cell of the present invention presents the peptide of the present invention on its surface and can strongly induce CTLs, so that the cell may be used as a CTL inducer and/or as a vaccine for the purpose of elimination of the SARS coronavirus. The antigen presenting cell is preferably prepared using a peptide at a concentration of preferably 1 to 100 µM, more preferably 5 to 50 µM, for example, 10 µM, per $10^7$ cells.

The peptide, the peptide-bound liposome and the antigen presenting cell of the present invention can be used as inducers of HLA-A2-restricted CTLs specific to the SARS coronavirus, and/or as vaccines for therapy or prophylaxis of infection of the SARS coronavirus. The subject may be any animal including human. In a certain mode, the subject is human. The inducer and/or vaccine of the present invention is/are made into a common form as a pharmaceutical composition depending on the substance regarded as the active ingredient, and direct delivery of the composition is generally achieved by parenteral injection (e.g., subcutaneous injection, intraperitoneal injection, intravenous injection, intramuscular injection, or injection to the space between tissues). Examples of other administration methods include mucosal administration (e.g., oral, transnasal or pulmonary), transocular administration, percutaneous administration and administration by suppositories.

That is, in cases where the composition is administered parenterally, it may be administered in a dosage form such as an injection solution, transnasal agent, formulation for topical administration (e.g., percutaneous preparation), or formulation for rectal administration. In cases where the composition is orally administered, it may be administered in a dosage form usually used in the art. Examples of the injection solution include sterile solutions or suspensions, and emulsions, and particular examples thereof include water, water-propylene glycol solutions, buffers and 0.4% physiological saline. Furthermore, in cases where the composition is made into a liquid formulation, it can be stored frozen, or stored after removing water by freeze-drying or the like. When the freeze-dried formulation is to be used, it can be used by adding distilled water for injection or the like thereto and redissolving it. Examples of the formulation for topical administration include creams, ointments, lotions and percutaneous preparations. Examples of the oral preparation or the formulation for rectal administration include capsules, tablets, pills, powders, drops, suppositories and liquids.

The above dosage forms are formulated by methods usually used in the art, together with pharmaceutically acceptable vehicles and additives. Examples of the pharmaceutically acceptable vehicles and additives include carriers, binders, flavoring agents, buffering agents, thickening agents, coloring agents, stabilizers, emulsifiers, dispersants, suspending agents, antiseptics, pH adjusting agents, tonicity adjusting agents and wetting agents. Furthermore, examples of the pharmaceutically acceptable carriers include magnesium carbonate, lactose, pectin, starch and methyl cellulose.

The inducer of the present invention containing as an active ingredient a peptide, a peptide-bound liposome or an antigen presenting cell, and the vaccine of the present invention containing as an active ingredient a peptide, a peptide-bound liposome or an antigen presenting cell may further contain an adjuvant for enhancement of its effect. Examples of the adjuvant include aluminum hydroxide gel, Freund's complete adjuvant, Freund's incomplete adjuvant, pertussis adjuvant, poly(I,C) and CpG-DNA. Among these, CpG-DNA is preferred. CpG-DNA is a DNA containing an unmethylated CpG motif, and it can activate dendritic cells and enhance the CTL induction by the peptide, peptide-bound liposome or antigen presenting cell of the present invention.

The dose of the peptide of the present invention in the formulation, and the number of doses of the formulation vary depending on the symptoms, age, body weight, dosage form and the like, and it is preferred to administer usually 0.01 µg to 1 mg, preferably 0.1 µg to 500 µg, more preferably 1.0 µg to 100 µg of the peptide once in every several days or several months. For example, for the primary immune response (that is, therapeutic or prophylactic administration), 1.0 μg to 500 μg of the peptide is administered to an adult patient, and depending on the response and the conditions of the patient assayed by measurement of the specific CTL activity in blood of the patient, boosting administration of 1.0 μg to 100 μg of the peptide is subsequently carried out according to boosting therapy that continues for several weeks to several months. The number of the antigen presenting cells of the present invention to be administered is preferably $10^9$ to $10^6$, more preferably $10^8$ to $10^7$, and the number of the cells may be appropriately controlled based on the symptoms, age, body weight, dosage form and the like.

EXAMPLES

The present invention will now be described more concretely, but the present invention is not restricted to the Examples below.

Example 1

Prediction of CTL Epitopes

Using two kinds of computer software for prediction of epitopes, BIMAS <http://www-bimas.cit.nih.gov/molbio/hla_bind>) and SYFPEITHI (<http://www.syfpeithi.de>), epitope candidates for pp1a were searched. The search was carried out with the following settings: HLA Molecule, HLA-A*0201; and Peptide Length, 9 to 10 amino acid residues. Thirty kinds of epitope candidate peptides showing high prediction scores in the both analytic methods were selected by the search. The amino acid sequences of these 30 kinds of epitope candidate peptides are shown in Table 1. For each of the 30 kinds of epitope candidate peptides, a synthetic peptide was prepared. Peptides that can actually function as epitopes were searched, and 9 kinds of epitopes were identified. In order to further analyze functions of the 9 kinds of peptides, the Examples 1 to 6 below were carried out.

TABLE 1

| Epitope | Sequence | SEQ ID No: | BIMAS | SYFPEITHI |
|---|---|---|---|---|
| 1) pp1a-15 | QLSLPVLQV | 1 | 160.0 | 26 |
| 2) pp1a-103 | TLGVLVPHV | 2 | 160.0 | 26 |
| 3) pp1a-445 | TLNEDLLEI | 3 | 98.4 | 28 |
| 4) pp1a-634 | KLSAGVEFL | 4 | 463.5 | 27 |
| 5) pp1a-651 | FLITGVFDI | 5 | 640.2 | 27 |
| 6) pp1a-1121 | ILLAPLLSA | 6 | 71.9 | 26 |
| 7) pp1a-1139 | SLQVCVQTV | 7 | 160.0 | 28 |
| 8) pp1a-1288 | MLSRALKKV | 8 | 272.0 | 25 |
| 9) pp1a-1652 | YLSSVLLAL | 9 | 226.0 | 28 |
| 10) pp1a-2187 | CLDAGINYV | 10 | 351.9 | 27 |
| 11) pp1a-2207 | AMWLLLLSI | 11 | 143.8 | 27 |
| 12) pp1a-2340 | WLMWFIISI | 12 | 1551.9 | 26 |
| 13) pp1a-2546 | ILLLDQVLV | 13 | 437.5 | 26 |
| 14) pp1a-2754 | TLLCVLAAL | 14 | 181.8 | 29 |

TABLE 1-continued

| Epitope | Sequence | SEQ ID No: | BIMAS | SYFPEITHI |
|---|---|---|---|---|
| 15) pp1a-2755 | LLCVLAALV | 15 | 118.2 | 25 |
| 16) pp1a-2758 | VLAALVCYI | 16 | 224.4 | 26 |
| 17) pp1a-2990 | ALSGVFCGV | 17 | 132.1 | 25 |
| 18) pp1a-3444 | VLAWLYAAV | 18 | 177.4 | 27 |
| 19) pp1a-3459 | FLNRFTTTL | 19 | 373.4 | 27 |
| 20) pp1a-3560 | MLLTFLTSL | 20 | 1174.4 | 29 |
| 21) pp1a-3564 | FLTSLLILV | 21 | 735.9 | 25 |
| 22) pp1a-3616 | FLLPSLATV | 22 | 2722.7 | 33 |
| 23) pp1a-3687 | TLMNVITLV | 23 | 591.9 | 25 |
| 24) pp1a-3709 | SMWALVISV | 24 | 958.9 | 28 |
| 25) pp1a-3730 | FLARAIVFV | 25 | 4047.2 | 29 |
| 26) pp1a-3745 | LLFITGNTL | 26 | 134.4 | 26 |
| 27) pp1a-3816 | KLNIKLLGI | 27 | 84.0 | 27 |
| 28) pp1a-3848 | VLLSVLQQL | 28 | 309.1 | 27 |
| 29) pp1a-4071 | ALWEIQQVV | 29 | 970.0 | 25 |
| 30) pp1a-4219 | VLGSLAATV | 30 | 118.2 | 26 |

Example 2

Measurement of Binding Affinity of Peptide to HLA-A*0201 Molecule

For the 30 kinds of epitope candidate peptides listed in Table 1, the binding affinity to HLA-A*0201, which is a major histocompatibility complex (MHC) class I molecule, was measured. The measurement was carried out using T2 cells, which are human lymphoid cells. T2 cells lack the TAP gene and hence cannot transport self-peptides derived from autoantigens. Therefore, these cells express HLA-A*0201, to which peptides are not bound, on the cell surfaces. When a peptide added to the outside of the cell is bound to HLA-A*0201, an HLA-A*0201 complex is formed and becomes stable. Using this principle, the binding affinity was calculated based on the relationship between the amount of the HLA-A*0201 complex formed and the concentration of the peptide added. As the antibody for detection of the HLA-A*0201 complex, an anti-HLA-A2 monoclonal antibody BB7.2 (ATCC) was used. Furthermore, an epitope of hepatitis C virus (NS3-1585) was used as a control.

More particularly, T2 cells were incubated at 37° C. overnight together with various concentrations of peptides. Thereafter, the cells were allowed to react with the anti-HLA-A2 antibody BB7.2, and then with a FITC-labeled secondary antibody, followed by analyzing the cells by flow cytometry. Using the mean fluorescence intensity (MFI) of the T2 cells pulsed with NS3-1585 as a standard (100%), the peptide concentration at which a mean fluorescence intensity of 50% was achieved was represented as $BL_{50}$ (half-maximal binding level) for each peptide and shown in Table 2. $BL_{50}$ values of less than 100 μM, 100 to 200 μM, and more than 200 μM were grouped into 3 categories "High", "Medium" and "Low", respectively, and 24 kinds of peptides showed high binding affinities.

TABLE 2

| Epitope | SEQ ID No: | BL$_{50}$ (μM) | Affinity |
|---|---|---|---|
| 1) pp1a-15 | 1 | 75.7 | High |
| 2) pp1a-103 | 2 | 3.1 | High |
| 3) pp1a-445 | 3 | 19.2 | High |
| 4) pp1a-634 | 4 | 59.8 | High |
| 5) pp1a-651 | 5 | 8.4 | High |
| 6) pp1a-1121 | 6 | 40.3 | High |
| 7) pp1a-1139 | 7 | 4.9 | High |
| 8) pp1a-1288 | 8 | 65.1 | High |
| 9) pp1a-1652 | 9 | 6.7 | High |
| 10) pp1a-2187 | 10 | 3.0 | High |
| 11) pp1a-2207 | 11 | 323.0 | Low |
| 12) pp1a-2340 | 12 | 2432.8 | Low |
| 13) pp1a-2546 | 13 | 7.6 | High |
| 14) pp1a-2754 | 14 | 96.7 | High |
| 15) pp1a-2755 | 15 | 187.2 | Medium |
| 16) pp1a-2758 | 16 | 97.3 | High |
| 17) pp1a-2990 | 17 | 6.2 | High |
| 18) pp1a-3444 | 18 | 53.0 | High |
| 19) pp1a-3459 | 19 | 39.6 | High |
| 20) pp1a-3560 | 20 | 47.1 | High |
| 21) pp1a-3564 | 21 | 100.4 | Medium |
| 22) pp1a-3616 | 22 | 31.8 | High |
| 23) pp1a-3687 | 23 | 22.8 | High |
| 24) pp1a-3709 | 24 | 6.4 | High |
| 25) pp1a-3730 | 25 | 25.7 | High |
| 26) pp1a-3745 | 26 | 153.7 | Medium |
| 27) pp1a-3816 | 27 | 68.1 | High |
| 28) pp1a-3848 | 28 | 102.5 | Medium |
| 29) pp1a-4071 | 29 | 8.3 | High |
| 30) pp1a-4219 | 30 | 53.3 | High |

Example 3

Induction of Peptide-Specific CTLs in Mice Immunized Using Antigen Presenting Cells Pulsed with Peptides In order to investigate whether or not CTLs are induced specifically to the 30 kinds of epitope candidate peptides listed in Table 1, mice were immunized with mouse spleen cells pulsed with the peptides in vitro, and the spleen cells were stimulated with the peptides followed by measuring the CTL induction activities. As the mouse, the HLA-A2 transgenic mouse (HDD II mouse, Institut Pasteur, France; provided by Dr. F. Lemonnier) prepared by knocking out mouse MHC class I and β2-microglobulin (β2-m) in a mouse and introducing HLA-A*0201, which is a type of human MHC class I, and the human β2-m gene was used. Using as an index the ratio of cells in which production of interferon-γ (IFN-γ) was promoted among CD8-positive cells, the CTL induction activity was measured.

Spleen cells prepared from a naive HLA-A2 transgenic mouse were incubated in vitro with each peptide at a concentration of 10 μM at 37° C. for hour. Another individual of a naive HLA-A2 transgenic mouse was immunized with the spleen cells pulsed with the peptide, by intravenous injection.

One week after the immunization, spleen cells were prepared from the immunized mouse, and the cells were suspended in a medium supplemented with 10% fetal calf serum (FCS), followed by plating the cells in a 96-well plate at the cell number of 2×10$^6$ cells/well. To each well, each peptide (10 μM, final concentration) and 5 μL of 25-fold diluted GOLGIPLUS™ solution (Japan BD) were added, and the resulting mixture was incubated at 37° C. for 5 hours. Here, GOLGIPLUS™ was used to inhibit secretion of produced IFN-γ by stopping intracellular transport. After washing the cells, 1 μg/10$^6$ cells of FcBlock antibody (Japan BD) suspended in 100 μL of FACS buffer (PBS containing 2% FCS and 0.1% sodium azide) was added to the cells and the resulting mixture was incubated at 4° C. for 10 minutes in order to suppress nonspecific reaction by blocking the Fc receptors on the cell surfaces.

Subsequently, for detecting CD8-positive cells, cells were stained by adding 0.5 μg of a fluorescein isothiocyanate (FITC)-labeled CD8 antibody to the cell suspension, and incubating the resulting mixture at 4° C. for 30 minutes, followed by washing the cells twice. Furthermore, using intracellular cytokine staining (ICS), IFN-γ in the cells was stained by the following procedure. First, 100 μL/well of CYTOFIX/CYTOPERM™ solution (Japan BD) was added to the cells, and the resulting mixture was left to stand at 4° C. for 20 minutes to fix the cells and permeabilize the cell membrane. The cells were washed twice, and then collected. Subsequently, 0.5 μg of a phycoerythrin (PE)-labeled anti-IFN-γ antibody was added to the cells, and the cells were incubated at 4° C. for 30 minutes. The cells were washed, and suspended in 100 μL of FACS fix buffer (PBS containing 2% FCS, 0.1% sodium azide and 1% formaldehyde), after which the cells were subjected to flow cytometry analysis.

For each epitope candidate peptide, the ratio (%) of IFN-γ-positive cells among CD8-positive cells is shown in Table 3.

TABLE 3

| Epitope | SEQ ID No: | ICS (% in CD8+ cells) |
|---|---|---|
| 1) pp1a-15 | 1 | 0.05 |
| 2) pp1a-103 | 2 | 0.07 |
| 3) pp1a-445 | 3 | 0.08 |
| 4) pp1a-634 | 4 | 0.08 |
| 5) pp1a-651 | 5 | 0.02 |
| 6) pp1a-1121 | 6 | 0.05 |
| 7) pp1a-1139 | 7 | 0.07 |
| 8) pp1a-1288 | 8 | 0.05 |
| 9) pp1a-1652 | 9 | 0.05 |
| 10) pp1a-2187 | 10 | *0.19 |
| 11) pp1a-2207 | 11 | *0.48 |
| 12) pp1a-2340 | 12 | *0.21 |
| 13) pp1a-2546 | 13 | *0.17 |
| 14) pp1a-2754 | 14 | 0.04 |
| 15) pp1a-2755 | 15 | *0.18 |
| 16) pp1a-2758 | 16 | 0.03 |
| 17) pp1a-2990 | 17 | *0.16 |
| 18) pp1a-3444 | 18 | *0.12 |
| 19) pp1a-3459 | 19 | 0.03 |
| 20) pp1a-3560 | 20 | 0.04 |
| 21) pp1a-3564 | 21 | 0.06 |
| 22) pp1a-3616 | 22 | 0.07 |
| 23) pp1a-3687 | 23 | *0.20 |
| 24) pp1a-3709 | 24 | *0.50 |
| 25) pp1a-3730 | 25 | 0.06 |
| 26) pp1a-3745 | 26 | 0.03 |
| 27) pp1a-3816 | 27 | 0.07 |
| 28) pp1a-3848 | 28 | 0.07 |
| 29) pp1a-4071 | 29 | 0.06 |
| 30) pp1a-4219 | 30 | 0.01 |

*ICS of 0.1% or more

As a result, among the 30 kinds of candidate peptides, 9 kinds of peptides (pp1a-2187, pp1a-2207, pp1a-2340, pp1a-2546, pp1a-2755, pp1a-2990, pp1a-3444, pp1a-3687 and pp1a-3709; SEQ ID NOs: 10, 11, 12, 13, 15, 17, 18, 23 and 24) significantly induced IFN-γ-positive cells among CD8-positive cells, so that these 9 kinds of peptides were determined as the epitopes. These included peptides having low binding affinities to HLA-A*0201 (pp1a-2207 and pp1a-2340) and a peptide having a medium binding affinity thereto (pp1a-2755), as shown in Example 2.

Example 4

Preparation of Liposomes and Peptide-Bound Liposomes

For the 9 kinds of CTL epitope peptides that showed especially high CTL induction activities in Example 3 (pp1a-2187, pp1a-2207, pp1a-2340, pp1a-2546, pp1a-2755, pp1a-2990, pp1a-3444, pp1a-3687 and pp1a-3709; SEQ ID NOs: 10, 11, 12, 13, 15, 17, 18, 23 and 24), peptide-bound liposomes were prepared by the following method. Furthermore, in the same manner, liposomes to which a helper peptide (amino acid sequence: TPPAYRPPNAPIL; SEQ ID NO:32) was bound were prepared. As the helper peptide, one synthesized based on the HBV core 128 helper peptide (Operon Biotechnologies) used by Dr. A. Sette et al. (e.g., Glenn Y et al., J. Immunol. 162:3915-3925 (1999)) was used.

(4-1) Synthesis of Reactive Phospholipid Composed of Terminally Modified Phosphatidylethanolamine (Succinimidyl Group-Dioleoylphosphatidylethanolamine)

In 50 ml of chloroform, 2 g of dioleoylphosphatidylethanolamine and 180 µl of triethylamine were dissolved/added, and the resulting solution was placed in a 300 ml four-necked flask. While stirring the solution in the flask with a magnetic stirrer at room temperature, a solution separately prepared by dissolving 3 g of disuccinimidyl suberate, which is a divalent reactive compound, in 80 ml of chloroform was added dropwise to the solution according to a conventional method for 4 hours, thereby allowing one terminus of disuccinimidyl suberate to react with the amino group of dioleoylphosphatidylethanolamine. This crude reaction solution was transferred to an eggplant type flask, and the solvent was evaporated with an evaporator. Subsequently, a small amount of chloroform which is enough for dissolving the crude reaction product was added to the flask to obtain a high concentration crude reaction product solution, and this solution was subjected to column chromatography according to a conventional method using silica gel equilibrated with chloroform/methanol/water (65/25/1, volume ratio). Only the fraction of interest that contained dioleoylphosphatidylethanolamine whose amino group is bound to one terminus of disuccinimidyl suberate was recovered, and the solvent was evaporated, to obtain the succinimidyl group-dioleoylphosphatidylethanolamine of interest.

(4-2) Preparation of Lipid Mixture Powder

In an eggplant type flask, 1.3354 g (1.6987 mmol) of dioleoylphosphatidylcholine, 0.2886 g (0.2831 mmol) of succinimidyl group-dioleoylphosphatidylethanolamine prepared in Example 4-1, 0.7663 g (1.9818 mmol) of cholesterol and 0.4513 g (0.5662 mmol) of dioleoylphosphatidylglycerol sodium salt were placed, and 50 ml of a chloroform/methanol/water (65/25/4, volume ratio)-mixed solvent was added thereto, followed by dissolving the reagents at 40° C. Subsequently, the solvent was evaporated under reduced pressure using a rotary evaporator, to prepare a thin lipid membrane. Furthermore, 30 ml of distilled water for injection was added thereto, and the resulting mixture was stirred, to obtain a uniform slurry. This slurry was frozen, and dried in a freeze dryer for 24 hours, to obtain a lipid mixture powder.

(4-3) Preparation of Liposomes

Subsequently, 60 ml of separately prepared buffer A (1.0 mM $Na_2HPO_4/KH_2PO_4$, 0.25 M saccharose, pH7.4) was placed in the eggplant type flask containing the lipid mixture powder, and the lipids were hydrated while stirring the resulting mixture at 40° C., thereby liposomes were obtained. Thereafter, the particle diameters of the liposomes were adjusted using an extruder. The liposomes were first allowed to pass through an 8-µm polycarbonate filter, and then through 5 µm, 3 µm, 1 µm, 0.65 µm, 0.4 µm and 0.2 µm filters in this order. As a result, liposome particles having an average particle diameter of 206 nm (measured by dynamic light scattering) were obtained.

(4-4) Preparation of Peptide-Bound Liposomes

In a 1.5 ml test tube, the liposomes obtained in Example 4-3 were collected, and 3 ml of each peptide solution (1.25 mM)/buffer A separately prepared was added thereto, followed by stirring the resulting mixture at 5° C. for 48 hours to allow the reaction to proceed. This reaction liquid was subjected to gel filtration according to a conventional method using Sepharose CL-4B equilibrated with buffer A. Since the liposome fraction is turbid, the fraction of interest can be easily recognized, but may also be confirmed using a UV detector or the like. The phosphorus concentration of the thus obtained liposome suspension was measured (Phospholipid Test, Wako), and the suspension was diluted with buffer A such that the concentration of phosphorus derived from the phospholipid is 2 mM, thereby obtaining a suspension of each peptide-bound liposome.

Example 5

Induction of Peptide-Specific CTLs in Mice Immunized Using Peptide-Bound Liposomes For the 9 kinds of CTL epitope peptides that showed especially high CTL induction activities in Example 3 (pp1a-2187, pp1a-2207, pp1a-2340, pp1a-2546, pp1a-2755, pp1a-2990, pp1a-3444, pp1a-3687 and pp1a-3709; SEQ ID NOs: 10, 11, 12, 13, 15, 17, 18, 23 and 24), the CTL induction activity in a mouse immunized using the peptide-bound liposome was measured.

A naive HLA-A2 transgenic mouse was immunized at its foot pad with an immunization solution obtained by mixing the peptide-bound liposomes (25 µl) and the helper peptide-bound liposomes prepared in Example 4 (25 µl) and an oligonucleic acid comprising a CpG motif (5 µg, base sequence: 5'-tccatgacgt tctgatgtt-3'; SEQ ID NO:33) together. After the immunization, the mouse was kept for 1 week, and the CTL induction activity was then measured by the same method as in Example 3. As a control, liposomes to which the peptide is not bound were used instead of the peptide-bound liposomes. As the oligonucleic acid comprising a CpG motif, one prepared by gene synthesis (Hokkaido System Science Co., Ltd.) based on Nagata. T. et al., Vaccine 25:4914-4921 (2007) was used.

Staining plots for CD8 and IFN-γ by flow cytometry in mice immunized using peptide-bound liposomes are shown in FIG. 1. Each dot inside the boxed area in the upper right of each graph corresponds to an IFN-γ-positive cell among CD8-positive cells, and the value shown in the boxed area indicates the ratio (%) of the IFN-γ-positive cells among the CD8-positive cells. As a result, it was revealed that immunization with the contained peptide-bound liposomes causes CTL induction.

Comparative Example

As a comparative control experiment for Example 5, the following experiment was carried out. Measurement of the CTL induction activity was carried out by the same method as in Example 4 except that, instead of a CTL epitope peptide of pp1a, a CTL epitope peptide of the Spike protein of SARS-CoV (spike-1203, amino acid sequence: FIAGLIAIV; SEQ ID NO:34) was used and that a naive HLA-A2 transgenic mouse was immunized by intramuscular injection at thigh muscle.

Staining plots for CD8 and IFN-γ by flow cytometry in mice immunized using the spike-1203-peptide-bound liposomes are shown in FIG. 2. As a result of the analysis, the ratio (%) of IFN-γ-positive cells among CD8-positive cells was 0.29 when the known CTL epitope peptide of the Spike protein (spike-1203) was used. When compared to the results in Example 4, it was revealed that 8 kinds of CTL epitope peptides derived from pp1a (pp1a-2187, pp1a-2207, pp1a-2340, pp1a-2546, pp1a-2755, pp1a-2990, pp1a-3687 and pp1a-3709; SEQ ID NOs: 10, 11, 12, 13, 15, 17, 23 and 24) show CTL induction activities higher than that of the CTL epitope peptide of the Spike protein.

Example 6

In Vivo CTL assay in Mice Immunized Using Peptide-Bound Liposomes

For 5 kinds of CTL epitope peptides that showed high CTL induction activities in Example 4 (pp1a-2187, pp1a-2340, pp1a-2755, pp1a-2990 and pp1a-3709; SEQ ID NOs: 10, 12, 15, 17 and 24), the CTL response activity in a mouse immunized using the peptide-bound liposome was measured in vivo.

The principle of measurement of the CTL response activity in vivo was as follows. Target cells which were not pulsed with the peptide (negative control) were labeled with carboxy fluorescein diacetate succinimidyl ester (CFSE) at a low concentration, and, on the other hand, target cells pulsed with the peptide were labeled with CFSE at a high concentration (10-fold). The same number of cells of the 2 kinds of cell populations were mixed together, and transferred to a mouse preliminarily immunized using the peptide-bound liposomes. Thereafter, spleen cells were collected from the mouse to which the mixed cells were transferred, and a spleen cell suspension was prepared, followed by measuring the ratio of the transferred cells labeled with CFSE by flow cytometry analysis. In a mouse having no CTL response activity to the antigen peptide, equal amounts of the CFSE-labeled transferred cells are collected. On the other hand, since, in a mouse having the CTL response activity to the antigen peptide, the target cells covered with the antigen peptide are lysed, the degree of the lysis in vivo can be measured by quantifying decrease in the cells highly labeled with CFSE by flow cytometry.

More particularly, the measurement was carried out by the following method.

A mouse for the transfer was preliminarily prepared by immunizing a mouse with the peptide-bound liposomes prepared using each peptide and inducing the peptide-specific CTLs. As a control, a mouse immunized with liposomes to which the peptide was not bound, instead of the peptide-bound liposomes, was used. One week after the immunization, spleen cells were prepared from another individual of the naive mouse, and the cells were suspended in RPMI-1640 (Sigma) at the cell number of the medium is $2\times10^8$ cells/2 mL. A 1 mL aliquot of the resulting suspension was taken into each of two tubes. To only one of the tubes, the peptide was added to a final concentration of 10 μM, and the two tubes were incubated at 37° C. for 1 to 2 hours. After washing the cells once, the cells were suspended in 20 mL of PBS/0.1% BSA and then briefly vortexed. Thereafter, to the tube containing the cells pulsed with the peptide, 10 μL of 5 mM CFSE was added, immediately followed by adding 1 μL of 5 mM CFSE to the tube containing the cells which were not incubated with the peptide. The both tubes were vortexed to suspend the cells, and incubated in a water bath at 37° C. for 10 minutes. The both cell populations were centrifuged and washed once, followed by counting the live cell numbers and suspending each cell population in HBSS to a concentration of $5\times10^7$ cells/mL. Equal amounts of the cell suspensions were mixed together to prepare an immunization liquid, and 200 μL ($1\times10^7$ cells/individual) of the resulting cell suspension was intravenously injected to a mouse preliminarily immunized, thereby carrying out the cell transfer. Twelve hours after the transfer, spleen cells were collected from the mouse, and suspended in 1 mL/spleen of PBS/1% FBS/5 mM EDTA. The cells were centrifuged and suspended in 1 mL of FACS fix buffer, and 100 μL of this spleen cell suspension was diluted with 2 mL of FACS buffer, followed by subjecting the resulting dilution to flow cytometry analysis.

Staining plots for CFSE by flow cytometry in mice to which the target cells labeled with CFSE were transferred are shown in FIG. 3. The rightmost peak in each graph indicates the cell population pulsed with the peptide, and the peak in its left indicates the cells which were not pulsed with the peptide. It was revealed that, in each CTL epitope peptide, the mouse immunized with the peptide-bound liposomes (right graph) shows a decreased number of the cells pulsed with the peptide compared to the control immunized with the liposomes (left graph). The peptide-specific lysis rates (%) of the target cells by CTLs were: pp1a-2187, 79.2%; pp1a-2340, 68.5%; pp1a-2755, 70.5%; pp1a-2990, 73.4%; and pp1a-3709, 96.3%; showing that all of these peptides have high CTL response activities. Among the peptides, pp1a-3709 was revealed to have an especially high CTL response activity. Therefore, it was revealed that these CTL epitope peptides (pp1a-2187, pp1a-2340, pp1a-2755, pp1a-2990 and pp1a-3709; SEQ ID NOs: 10, 12, 15, 17 and 24) are dominant peptides having high CTL response activities.

The invention claimed is:

1. A peptide-bound liposome, wherein the peptide is covalently bound to the surface of the liposome; the liposome comprises: a phospholipid comprising a $C_{14}$-$C_{24}$ acyl group containing one unsaturated bond, or a $C_{14}$-$C_{24}$ hydrocarbon group containing one unsaturated bond, and a stabilizer; and the peptide comprises the amino acid sequence of SEQ ID NO: 24, wherein the peptide-bound liposome induces an immune response that produces human leukocyte antigen type A2 (HLA-A2)-restricted cytotoxic T lymphocytes (CTLs) specific to severe acute respiratory syndrome (SARS) coronavirus.

2. The peptide-bound liposome according to claim 1, wherein the phospholipid comprises a $C_{14}$-$C_{24}$ acyl group containing one unsaturated bond.

3. The peptide-bound liposome according to claim 1, wherein the phospholipid comprises an oleoyl group.

4. The peptide-bound liposome according to claim 1, wherein the phospholipid is at least one selected from the group consisting of diacylphosphatidylserine, diacylphosphatidylglycerol, diacylphosphatidic acid, diacylphosphatidylcholine, diacylphosphatidylethanolamine, succinimidyl-diacylphosphatidylethanolamine and maleimide-diacylphosphatidylethanolamine.

5. The peptide-bound liposome according to claim 1, wherein the stabilizer is cholesterol.

6. The peptide-bound liposome according to claim 1, wherein the peptide is covalently bound to the phospholipid on the surface of the liposome.

7. The peptide-bound liposome according to claim 1, wherein the liposome comprises:

(A) 1 to 99.8 mol % of a phospholipid comprising:
a $C_{14}$-$C_{24}$ acyl group containing one unsaturated bond, or a $C_{14}$-$C_{24}$ hydrocarbon group containing one unsaturated bond; and (B) 0.2 to 75 mol % of a stabilizer.

8. A peptide-bound liposome according to claim 1 comprising:

(I) 1 to 85 mol % of an acidic phospholipid comprising a $C_{14}$-$C_{24}$ acyl group containing one unsaturated bond, or a $C_{14}$-$C_{24}$ hydrocarbon group containing one unsaturated bond;

(II) 0.01 to 80 mol % of a neutral phospholipid comprising a $C_{14}$-$C_{24}$ acyl group containing one unsaturated bond, or a $C_{14}$-$C_{24}$ hydrocarbon group containing one unsaturated bond;

(III) 0.2 to 80 mol % of a phospholipid comprising a $C_{14}$-$C_{24}$ acyl group containing one unsaturated bond, or a $C_{14}$-$C_{24}$ hydrocarbon group containing one unsaturated bond, wherein the phospholipid is bound to the at least one peptide; and (IV) 0.2 to 75 mol % of a stabilizer.

9. An inducing agent for human leukocyte antigen type A2 (HLA-A2)-restricted cytotoxic T lymphocytes (CTLs) specific to severe acute respiratory syndrome (SARS) coronavirus comprising: the peptide-bound liposome according to claim 1 as an active ingredient, and a pharmaceutically acceptable carrier, wherein the agent induces an immune response that produces HLA-A2-restricted CTLs specific to SARS coronavirus.

10. A vaccine comprising: the peptide-bound liposome according to claim 1, and a pharmaceutically acceptable carrier, wherein the vaccine induces an immune response that produces HLA-A2-restricted CTLs specific to SARS coronavirus.

11. The inducing agent for HLA-A2-restricted CTLs specific to the SARS coronavirus according to claim 9, further comprising CpG-DNA.

12. The vaccine according to claim 10, further comprising CpG-DNA.

13. A method of producing an immune response to severe acute respiratory syndrome (SARS) coronavirus in a subject, comprising administering to the subject an effective amount of the vaccine composition of claim 10, thereby inducing the immune response to SARS coronavirus in the subject.

14. The method of claim 13, wherein the subject is human.

* * * * *

SEQUENCE LISTING

```
<160> NUMBER OF SEQ ID NOS: 34

<210> SEQ ID NO 1
<211> LENGTH: 9
<212> TYPE: PRT
<213> ORGANISM: SARS coronavirus

<400> SEQUENCE: 1

Gln Leu Ser Leu Pro Val Leu Gln Val
```

1               5

<210> SEQ ID NO 2
<211> LENGTH: 9
<212> TYPE: PRT
<213> ORGANISM: SARS coronavirus

<400> SEQUENCE: 2

Thr Leu Gly Val Leu Val Pro His Val
1               5

<210> SEQ ID NO 3
<211> LENGTH: 9
<212> TYPE: PRT
<213> ORGANISM: SARS coronavirus

<400> SEQUENCE: 3

Thr Leu Asn Glu Asp Leu Leu Glu Ile
1               5

<210> SEQ ID NO 4
<211> LENGTH: 9
<212> TYPE: PRT
<213> ORGANISM: SARS coronavirus

<400> SEQUENCE: 4

Lys Leu Ser Ala Gly Val Glu Phe Leu
1               5

<210> SEQ ID NO 5
<211> LENGTH: 9
<212> TYPE: PRT
<213> ORGANISM: SARS coronavirus

<400> SEQUENCE: 5

Phe Leu Ile Thr Gly Val Phe Asp Ile
1               5

<210> SEQ ID NO 6
<211> LENGTH: 9
<212> TYPE: PRT
<213> ORGANISM: SARS coronavirus

<400> SEQUENCE: 6

Ile Leu Leu Ala Pro Leu Leu Ser Ala
1               5

<210> SEQ ID NO 7
<211> LENGTH: 9
<212> TYPE: PRT
<213> ORGANISM: SARS coronavirus

<400> SEQUENCE: 7

Ser Leu Gln Val Cys Val Gln Thr Val
1               5

<210> SEQ ID NO 8
<211> LENGTH: 9
<212> TYPE: PRT
<213> ORGANISM: SARS coronavirus

<400> SEQUENCE: 8

Met Leu Ser Arg Ala Leu Lys Lys Val
1               5

<210> SEQ ID NO 9
<211> LENGTH: 9
<212> TYPE: PRT
<213> ORGANISM: SARS coronavirus

<400> SEQUENCE: 9

Tyr Leu Ser Ser Val Leu Leu Ala Leu
1               5

<210> SEQ ID NO 10
<211> LENGTH: 9
<212> TYPE: PRT
<213> ORGANISM: SARS coronavirus

<400> SEQUENCE: 10

Cys Leu Asp Ala Gly Ile Asn Tyr Val
1               5

<210> SEQ ID NO 11
<211> LENGTH: 9
<212> TYPE: PRT
<213> ORGANISM: SARS coronavirus

<400> SEQUENCE: 11

Ala Met Trp Leu Leu Leu Leu Ser Ile
1               5

<210> SEQ ID NO 12
<211> LENGTH: 9
<212> TYPE: PRT
<213> ORGANISM: SARS coronavirus

<400> SEQUENCE: 12

Trp Leu Met Trp Phe Ile Ile Ser Ile
1               5

<210> SEQ ID NO 13
<211> LENGTH: 9
<212> TYPE: PRT
<213> ORGANISM: SARS coronavirus

<400> SEQUENCE: 13

Ile Leu Leu Leu Asp Gln Val Leu Val
1               5

<210> SEQ ID NO 14
<211> LENGTH: 9
<212> TYPE: PRT
<213> ORGANISM: SARS coronavirus

<400> SEQUENCE: 14

Thr Leu Leu Cys Val Leu Ala Ala Leu
1               5

<210> SEQ ID NO 15
<211> LENGTH: 9
<212> TYPE: PRT
<213> ORGANISM: SARS coronavirus

<400> SEQUENCE: 15

Leu Leu Cys Val Leu Ala Ala Leu Val
1               5

<210> SEQ ID NO 16

```
<211> LENGTH: 9
<212> TYPE: PRT
<213> ORGANISM: SARS coronavirus

<400> SEQUENCE: 16

Val Leu Ala Ala Leu Val Cys Tyr Ile
1               5

<210> SEQ ID NO 17
<211> LENGTH: 9
<212> TYPE: PRT
<213> ORGANISM: SARS coronavirus

<400> SEQUENCE: 17

Ala Leu Ser Gly Val Phe Cys Gly Val
1               5

<210> SEQ ID NO 18
<211> LENGTH: 9
<212> TYPE: PRT
<213> ORGANISM: SARS coronavirus

<400> SEQUENCE: 18

Val Leu Ala Trp Leu Tyr Ala Ala Val
1               5

<210> SEQ ID NO 19
<211> LENGTH: 9
<212> TYPE: PRT
<213> ORGANISM: SARS coronavirus

<400> SEQUENCE: 19

Phe Leu Asn Arg Phe Thr Thr Thr Leu
1               5

<210> SEQ ID NO 20
<211> LENGTH: 9
<212> TYPE: PRT
<213> ORGANISM: SARS coronavirus

<400> SEQUENCE: 20

Met Leu Leu Thr Phe Leu Thr Ser Leu
1               5

<210> SEQ ID NO 21
<211> LENGTH: 9
<212> TYPE: PRT
<213> ORGANISM: SARS coronavirus

<400> SEQUENCE: 21

Phe Leu Thr Ser Leu Leu Ile Leu Val
1               5

<210> SEQ ID NO 22
<211> LENGTH: 9
<212> TYPE: PRT
<213> ORGANISM: SARS coronavirus

<400> SEQUENCE: 22

Phe Leu Leu Pro Ser Leu Ala Thr Val
1               5

<210> SEQ ID NO 23
<211> LENGTH: 9
<212> TYPE: PRT
```

-continued

<213> ORGANISM: SARS coronavirus

<400> SEQUENCE: 23

Thr Leu Met Asn Val Ile Thr Leu Val
1               5

<210> SEQ ID NO 24
<211> LENGTH: 9
<212> TYPE: PRT
<213> ORGANISM: SARS coronavirus

<400> SEQUENCE: 24

Ser Met Trp Ala Leu Val Ile Ser Val
1               5

<210> SEQ ID NO 25
<211> LENGTH: 9
<212> TYPE: PRT
<213> ORGANISM: SARS coronavirus

<400> SEQUENCE: 25

Phe Leu Ala Arg Ala Ile Val Phe Val
1               5

<210> SEQ ID NO 26
<211> LENGTH: 9
<212> TYPE: PRT
<213> ORGANISM: SARS coronavirus

<400> SEQUENCE: 26

Leu Leu Phe Ile Thr Gly Asn Thr Leu
1               5

<210> SEQ ID NO 27
<211> LENGTH: 9
<212> TYPE: PRT
<213> ORGANISM: SARS coronavirus

<400> SEQUENCE: 27

Lys Leu Asn Ile Lys Leu Leu Gly Ile
1               5

<210> SEQ ID NO 28
<211> LENGTH: 9
<212> TYPE: PRT
<213> ORGANISM: SARS coronavirus

<400> SEQUENCE: 28

Val Leu Leu Ser Val Leu Gln Gln Leu
1               5

<210> SEQ ID NO 29
<211> LENGTH: 9
<212> TYPE: PRT
<213> ORGANISM: SARS coronavirus

<400> SEQUENCE: 29

Ala Leu Trp Glu Ile Gln Gln Val Val
1               5

<210> SEQ ID NO 30
<211> LENGTH: 9
<212> TYPE: PRT
<213> ORGANISM: SARS coronavirus -continued

<400> SEQUENCE: 30

Val Leu Gly Ser Leu Ala Ala Thr Val
1 5

<210> SEQ ID NO 31
<211> LENGTH: 4382
<212> TYPE: PRT
<213> ORGANISM: SARS coronavirus

<400> SEQUENCE: 31

Met Glu Ser Leu Val Leu Gly Val Asn Glu Lys Thr His Val Gln Leu
1 5 10 15

Ser Leu Pro Val Leu Gln Val Arg Asp Val Leu Val Arg Gly Phe Gly
20 25 30

Asp Ser Val Glu Glu Ala Leu Ser Glu Ala Arg Glu His Leu Lys Asn
35 40 45

Gly Thr Cys Gly Leu Val Glu Leu Glu Lys Gly Val Leu Pro Gln Leu
50 55 60

Glu Gln Pro Tyr Val Phe Ile Lys Arg Ser Asp Ala Leu Ser Thr Asn
65 70 75 80

His Gly His Lys Val Val Glu Leu Val Ala Glu Met Asp Gly Ile Gln
85 90 95

Tyr Gly Arg Ser Gly Ile Thr Leu Gly Val Leu Val Pro His Val Gly
100 105 110

Glu Thr Pro Ile Ala Tyr Arg Asn Val Leu Leu Arg Lys Asn Gly Asn
115 120 125

Lys Gly Ala Gly Gly His Ser Tyr Gly Ile Asp Leu Lys Ser Tyr Asp
130 135 140

Leu Gly Asp Glu Leu Gly Thr Asp Pro Ile Glu Asp Tyr Glu Gln Asn
145 150 155 160

Trp Asn Thr Lys His Gly Ser Gly Ala Leu Arg Glu Leu Thr Arg Glu
165 170 175

Leu Asn Gly Gly Ala Val Thr Arg Tyr Val Asp Asn Asn Phe Cys Gly
180 185 190

Pro Asp Gly Tyr Pro Leu Asp Cys Ile Lys Asp Phe Leu Ala Arg Ala
195 200 205

Gly Lys Ser Met Cys Thr Leu Ser Glu Gln Leu Asp Tyr Ile Glu Ser
210 215 220

Lys Arg Gly Val Tyr Cys Cys Arg Asp His Glu His Glu Ile Ala Trp
225 230 235 240

Phe Thr Glu Arg Ser Asp Lys Ser Tyr Glu His Gln Thr Pro Phe Glu
245 250 255

Ile Lys Ser Ala Lys Lys Phe Asp Thr Phe Lys Gly Glu Cys Pro Lys
260 265 270

Phe Val Phe Pro Leu Asn Ser Lys Val Lys Val Ile Gln Pro Arg Val
275 280 285

Glu Lys Lys Lys Thr Glu Gly Phe Met Gly Arg Ile Arg Ser Val Tyr
290 295 300

Pro Val Ala Ser Pro Gln Glu Cys Asn Asn Met His Leu Ser Thr Leu
305 310 315 320

Met Lys Cys Asn His Cys Asp Glu Val Ser Trp Gln Thr Cys Asp Phe
325 330 335

Leu Lys Ala Thr Cys Glu His Cys Gly Thr Glu Asn Leu Val Ile Glu
340 345 350

-continued

Gly Pro Thr Thr Cys Gly Tyr Leu Pro Thr Asn Ala Val Val Lys Met
            355                 360                 365
Pro Cys Pro Ala Cys Gln Asp Pro Glu Ile Gly Pro Glu His Ser Val
370                 375                 380
Ala Asp Tyr His Asn His Ser Asn Ile Glu Thr Arg Leu Arg Lys Gly
385                 390                 395                 400
Gly Arg Thr Arg Cys Phe Gly Gly Cys Val Phe Ala Tyr Val Gly Cys
                405                 410                 415
Tyr Asn Lys Arg Ala Tyr Trp Val Pro Arg Ala Ser Ala Asp Ile Gly
                420                 425                 430
Ser Gly His Thr Gly Ile Thr Gly Asp Asn Val Glu Thr Leu Asn Glu
            435                 440                 445
Asp Leu Leu Glu Ile Leu Ser Arg Glu Arg Val Asn Ile Asn Ile Val
450                 455                 460
Gly Asp Phe His Leu Asn Glu Glu Val Ala Ile Ile Leu Ala Ser Phe
465                 470                 475                 480
Ser Ala Ser Thr Ser Ala Phe Ile Asp Thr Ile Lys Ser Leu Asp Tyr
                485                 490                 495
Lys Ser Phe Lys Thr Ile Val Glu Ser Cys Gly Asn Tyr Lys Val Thr
            500                 505                 510
Lys Gly Lys Pro Val Lys Gly Ala Trp Asn Ile Gly Gln Gln Arg Ser
            515                 520                 525
Val Leu Thr Pro Leu Cys Gly Phe Pro Ser Gln Ala Ala Gly Val Ile
            530                 535                 540
Arg Ser Ile Phe Ala Arg Thr Leu Asp Ala Ala Asn His Ser Ile Pro
545                 550                 555                 560
Asp Leu Gln Arg Ala Ala Val Thr Ile Leu Asp Gly Ile Ser Glu Gln
                565                 570                 575
Ser Leu Arg Leu Val Asp Ala Met Val Tyr Thr Ser Asp Leu Leu Thr
            580                 585                 590
Asn Ser Val Ile Ile Met Ala Tyr Val Thr Gly Gly Leu Val Gln Gln
            595                 600                 605
Thr Ser Gln Trp Leu Ser Asn Leu Leu Gly Thr Thr Val Glu Lys Leu
            610                 615                 620
Arg Pro Ile Phe Glu Trp Ile Glu Ala Lys Leu Ser Ala Gly Val Glu
625                 630                 635                 640
Phe Leu Lys Asp Ala Trp Glu Ile Leu Lys Phe Leu Ile Thr Gly Val
                645                 650                 655
Phe Asp Ile Val Lys Gly Gln Ile Gln Val Ala Ser Asp Asn Ile Lys
            660                 665                 670
Asp Cys Val Lys Cys Phe Ile Asp Val Val Asn Lys Ala Leu Glu Met
            675                 680                 685
Cys Ile Asp Gln Val Thr Ile Ala Gly Ala Lys Leu Arg Ser Leu Asn
            690                 695                 700
Leu Gly Glu Val Phe Ile Ala Gln Ser Lys Gly Leu Tyr Arg Gln Cys
705                 710                 715                 720
Ile Arg Gly Lys Glu Gln Leu Gln Leu Leu Met Pro Leu Lys Ala Pro
                725                 730                 735
Lys Glu Val Thr Phe Leu Glu Gly Asp Ser His Asp Thr Val Leu Thr
            740                 745                 750
Ser Glu Glu Val Val Leu Lys Asn Gly Glu Leu Glu Ala Leu Glu Thr
            755                 760                 765
Pro Val Asp Ser Phe Thr Asn Gly Ala Ile Val Gly Thr Pro Val Cys

```
                770                 775                 780
Val Asn Gly Leu Met Leu Leu Glu Ile Lys Asp Lys Glu Gln Tyr Cys
785                 790                 795                 800

Ala Leu Ser Pro Gly Leu Leu Ala Thr Asn Asn Val Phe Arg Leu Lys
                805                 810                 815

Gly Gly Ala Pro Ile Lys Gly Val Thr Phe Gly Glu Asp Thr Val Trp
                820                 825                 830

Glu Val Gln Gly Tyr Lys Asn Val Arg Ile Thr Phe Glu Leu Asp Glu
                835                 840                 845

Arg Val Asp Lys Val Leu Asn Glu Lys Cys Ser Val Tyr Thr Val Glu
                850                 855                 860

Ser Gly Thr Glu Val Thr Glu Phe Ala Cys Val Val Ala Glu Ala Val
865                 870                 875                 880

Val Lys Thr Leu Gln Pro Val Ser Asp Leu Leu Thr Asn Met Gly Ile
                885                 890                 895

Asp Leu Asp Glu Trp Ser Val Ala Thr Phe Tyr Leu Phe Asp Asp Ala
                900                 905                 910

Gly Glu Glu Asn Phe Ser Ser Arg Met Tyr Cys Ser Phe Tyr Pro Pro
                915                 920                 925

Asp Glu Glu Glu Asp Asp Ala Glu Cys Glu Glu Glu Glu Ile Asp
                930                 935                 940

Glu Thr Cys Glu His Glu Tyr Gly Thr Glu Asp Asp Tyr Gln Gly Leu
945                 950                 955                 960

Pro Leu Glu Phe Gly Ala Ser Ala Glu Thr Val Arg Val Glu Glu Glu
                965                 970                 975

Glu Glu Glu Asp Trp Leu Asp Asp Thr Thr Glu Gln Ser Glu Ile Glu
                980                 985                 990

Pro Glu Pro Glu Pro Thr Pro Glu Pro Val Asn Gln Phe Thr Gly
                995                 1000                1005

Tyr Leu Lys Leu Thr Asp Asn Val Ala Ile Lys Cys Val Asp Ile
        1010                1015                1020

Val Lys Glu Ala Gln Ser Ala Asn Pro Met Val Ile Val Asn Ala
        1025                1030                1035

Ala Asn Ile His Leu Lys His Gly Gly Gly Val Ala Gly Ala Leu
        1040                1045                1050

Asn Lys Ala Thr Asn Gly Ala Met Gln Lys Glu Ser Asp Asp Tyr
        1055                1060                1065

Ile Lys Leu Asn Gly Pro Leu Thr Val Gly Gly Ser Cys Leu Leu
        1070                1075                1080

Ser Gly His Asn Leu Ala Lys Lys Cys Leu His Val Val Gly Pro
        1085                1090                1095

Asn Leu Asn Ala Gly Glu Asp Ile Gln Leu Leu Lys Ala Ala Tyr
        1100                1105                1110

Glu Asn Phe Asn Ser Gln Asp Ile Leu Leu Ala Pro Leu Leu Ser
        1115                1120                1125

Ala Gly Ile Phe Gly Ala Lys Pro Leu Gln Ser Leu Gln Val Cys
        1130                1135                1140

Val Gln Thr Val Arg Thr Gln Val Tyr Ile Ala Val Asn Asp Lys
        1145                1150                1155

Ala Leu Tyr Glu Gln Val Val Met Asp Tyr Leu Asp Asn Leu Lys
        1160                1165                1170

Pro Arg Val Glu Ala Pro Lys Gln Glu Glu Pro Pro Asn Thr Glu
        1175                1180                1185
```

-continued

Asp Ser Lys Thr Glu Glu Lys Ser Val Val Gln Lys Pro Val Asp
    1190            1195                1200

Val Lys Pro Lys Ile Lys Ala Cys Ile Asp Glu Val Thr Thr Thr
    1205            1210                1215

Leu Glu Glu Thr Lys Phe Leu Thr Asn Lys Leu Leu Phe Ala
    1220            1225                1230

Asp Ile Asn Gly Lys Leu Tyr His Asp Ser Gln Asn Met Leu Arg
    1235            1240                1245

Gly Glu Asp Met Ser Phe Leu Glu Lys Asp Ala Pro Tyr Met Val
    1250            1255                1260

Gly Asp Val Ile Thr Ser Gly Asp Ile Thr Cys Val Val Ile Pro
    1265            1270                1275

Ser Lys Lys Ala Gly Gly Thr Thr Glu Met Leu Ser Arg Ala Leu
    1280            1285                1290

Lys Lys Val Pro Val Asp Glu Tyr Ile Thr Thr Tyr Pro Gly Gln
    1295            1300                1305

Gly Cys Ala Gly Tyr Thr Leu Glu Glu Ala Lys Thr Ala Leu Lys
    1310            1315                1320

Lys Cys Lys Ser Ala Phe Tyr Val Leu Pro Ser Glu Ala Pro Asn
    1325            1330                1335

Ala Lys Glu Glu Ile Leu Gly Thr Val Ser Trp Asn Leu Arg Glu
    1340            1345                1350

Met Leu Ala His Ala Glu Glu Thr Arg Lys Leu Met Pro Ile Cys
    1355            1360                1365

Met Asp Val Arg Ala Ile Met Ala Thr Ile Gln Arg Lys Tyr Lys
    1370            1375                1380

Gly Ile Lys Ile Gln Glu Gly Ile Val Asp Tyr Gly Val Arg Phe
    1385            1390                1395

Phe Phe Tyr Thr Ser Lys Glu Pro Val Ala Ser Ile Ile Thr Lys
    1400            1405                1410

Leu Asn Ser Leu Asn Glu Pro Leu Val Thr Met Pro Ile Gly Tyr
    1415            1420                1425

Val Thr His Gly Phe Asn Leu Glu Glu Ala Ala Arg Cys Met Arg
    1430            1435                1440

Ser Leu Lys Ala Pro Ala Val Val Ser Val Ser Ser Pro Asp Ala
    1445            1450                1455

Val Thr Thr Tyr Asn Gly Tyr Leu Thr Ser Ser Ser Lys Thr Ser
    1460            1465                1470

Glu Glu His Phe Val Glu Thr Val Ser Leu Ala Gly Ser Tyr Arg
    1475            1480                1485

Asp Trp Ser Tyr Ser Gly Gln Arg Thr Glu Leu Gly Val Glu Phe
    1490            1495                1500

Leu Lys Arg Gly Asp Lys Ile Val Tyr His Thr Leu Glu Ser Pro
    1505            1510                1515

Val Glu Phe His Leu Asp Gly Glu Val Leu Ser Leu Asp Lys Leu
    1520            1525                1530

Lys Ser Leu Leu Ser Leu Arg Glu Val Lys Thr Ile Lys Val Phe
    1535            1540                1545

Thr Thr Val Asp Asn Thr Asn Leu His Thr Gln Leu Val Asp Met
    1550            1555                1560

Ser Met Thr Tyr Gly Gln Gln Phe Gly Pro Thr Tyr Leu Asp Gly
    1565            1570                1575

-continued

| | | | | | | | | | | | |
|---|---|---|---|---|---|---|---|---|---|---|---|
| Ala | Asp | Val | Thr | Lys | Ile | Lys | Pro | His | Val | Asn | His | Glu | Gly | Lys |
| 1580 | | | | | 1585 | | | | | 1590 | | | | |

Thr Phe Phe Val Leu Pro Ser Asp Asp Thr Leu Arg Ser Glu Ala
1595 1600 1605

Phe Glu Tyr Tyr His Thr Leu Asp Glu Ser Phe Leu Gly Arg Tyr
1610 1615 1620

Met Ser Ala Leu Asn His Thr Lys Lys Trp Lys Phe Pro Gln Val
1625 1630 1635

Gly Gly Leu Thr Ser Ile Lys Trp Ala Asp Asn Asn Cys Tyr Leu
1640 1645 1650

Ser Ser Val Leu Leu Ala Leu Gln Gln Leu Glu Val Lys Phe Asn
1655 1660 1665

Ala Pro Ala Leu Gln Glu Ala Tyr Tyr Arg Ala Arg Ala Gly Asp
1670 1675 1680

Ala Ala Asn Phe Cys Ala Leu Ile Leu Ala Tyr Ser Asn Lys Thr
1685 1690 1695

Val Gly Glu Leu Gly Asp Val Arg Glu Thr Met Thr His Leu Leu
1700 1705 1710

Gln His Ala Asn Leu Glu Ser Ala Lys Arg Val Leu Asn Val Val
1715 1720 1725

Cys Lys His Cys Gly Gln Lys Thr Thr Thr Leu Thr Gly Val Glu
1730 1735 1740

Ala Val Met Tyr Met Gly Thr Leu Ser Tyr Asp Asn Leu Lys Thr
1745 1750 1755

Gly Val Ser Ile Pro Cys Val Cys Gly Arg Asp Ala Thr Gln Tyr
1760 1765 1770

Leu Val Gln Gln Glu Ser Ser Phe Val Met Met Ser Ala Pro Pro
1775 1780 1785

Ala Glu Tyr Lys Leu Gln Gln Gly Thr Phe Leu Cys Ala Asn Glu
1790 1795 1800

Tyr Thr Gly Asn Tyr Gln Cys Gly His Tyr Thr His Ile Thr Ala
1805 1810 1815

Lys Glu Thr Leu Tyr Arg Ile Asp Gly Ala His Leu Thr Lys Met
1820 1825 1830

Ser Glu Tyr Lys Gly Pro Val Thr Asp Val Phe Tyr Lys Glu Thr
1835 1840 1845

Ser Tyr Thr Thr Thr Ile Lys Pro Val Ser Tyr Lys Leu Asp Gly
1850 1855 1860

Val Thr Tyr Thr Glu Ile Glu Pro Lys Leu Asp Gly Tyr Tyr Lys
1865 1870 1875

Lys Asp Asn Ala Tyr Tyr Thr Glu Gln Pro Ile Asp Leu Val Pro
1880 1885 1890

Thr Gln Pro Leu Pro Asn Ala Ser Phe Asp Asn Phe Lys Leu Thr
1895 1900 1905

Cys Ser Asn Thr Lys Phe Ala Asp Asp Leu Asn Gln Met Thr Gly
1910 1915 1920

Phe Thr Lys Pro Ala Ser Arg Glu Leu Ser Val Thr Phe Phe Pro
1925 1930 1935

Asp Leu Asn Gly Asp Val Val Ala Ile Asp Tyr Arg His Tyr Ser
1940 1945 1950

Ala Ser Phe Lys Lys Gly Ala Lys Leu Leu His Lys Pro Ile Val
1955 1960 1965

Trp His Ile Asn Gln Ala Thr Thr Lys Thr Thr Phe Lys Pro Asn

-continued

```
             1970                1975                1980
Thr Trp Cys Leu Arg Cys Leu Trp Ser Thr Lys Pro Val Asp Thr
     1985                1990                1995
Ser Asn Ser Phe Glu Val Leu Ala Val Glu Asp Thr Gln Gly Met
     2000                2005                2010
Asp Asn Leu Ala Cys Glu Ser Gln Gln Pro Thr Ser Glu Glu Val
     2015                2020                2025
Val Glu Asn Pro Thr Ile Gln Lys Glu Val Ile Glu Cys Asp Val
     2030                2035                2040
Lys Thr Thr Glu Val Val Gly Asn Val Ile Leu Lys Pro Ser Asp
     2045                2050                2055
Glu Gly Val Lys Val Thr Gln Glu Leu Gly His Glu Asp Leu Met
     2060                2065                2070
Ala Ala Tyr Val Glu Asn Thr Ser Ile Thr Ile Lys Lys Pro Asn
     2075                2080                2085
Glu Leu Ser Leu Ala Leu Gly Leu Lys Thr Ile Ala Thr His Gly
     2090                2095                2100
Ile Ala Ala Ile Asn Ser Val Pro Trp Ser Lys Ile Leu Ala Tyr
     2105                2110                2115
Val Lys Pro Phe Leu Gly Gln Ala Ala Ile Thr Thr Ser Asn Cys
     2120                2125                2130
Ala Lys Arg Leu Ala Gln Arg Val Phe Asn Asn Tyr Met Pro Tyr
     2135                2140                2145
Val Phe Thr Leu Leu Phe Gln Leu Cys Thr Phe Thr Lys Ser Thr
     2150                2155                2160
Asn Ser Arg Ile Arg Ala Ser Leu Pro Thr Thr Ile Ala Lys Asn
     2165                2170                2175
Ser Val Lys Ser Val Ala Lys Leu Cys Leu Asp Ala Gly Ile Asn
     2180                2185                2190
Tyr Val Lys Ser Pro Lys Phe Ser Lys Leu Phe Thr Ile Ala Met
     2195                2200                2205
Trp Leu Leu Leu Leu Ser Ile Cys Leu Gly Ser Leu Ile Cys Val
     2210                2215                2220
Thr Ala Ala Phe Gly Val Leu Leu Ser Asn Phe Gly Ala Pro Ser
     2225                2230                2235
Tyr Cys Asn Gly Val Arg Glu Leu Tyr Leu Asn Ser Ser Asn Val
     2240                2245                2250
Thr Thr Met Asp Phe Cys Glu Gly Ser Phe Pro Cys Ser Ile Cys
     2255                2260                2265
Leu Ser Gly Leu Asp Ser Leu Asp Ser Tyr Pro Ala Leu Glu Thr
     2270                2275                2280
Ile Gln Val Thr Ile Ser Ser Tyr Lys Leu Asp Leu Thr Ile Leu
     2285                2290                2295
Gly Leu Ala Ala Glu Trp Val Leu Ala Tyr Met Leu Phe Thr Lys
     2300                2305                2310
Phe Phe Tyr Leu Leu Gly Leu Ser Ala Ile Met Gln Val Phe Phe
     2315                2320                2325
Gly Tyr Phe Ala Ser His Phe Ile Ser Asn Ser Trp Leu Met Trp
     2330                2335                2340
Phe Ile Ile Ser Ile Val Gln Met Ala Pro Val Ser Ala Met Val
     2345                2350                2355
Arg Met Tyr Ile Phe Phe Ala Ser Phe Tyr Tyr Ile Trp Lys Ser
     2360                2365                2370
```

```
Tyr Val His Ile Met Asp Gly Cys Thr Ser Ser Thr Cys Met Met
2375                2380                2385

Cys Tyr Lys Arg Asn Arg Ala Thr Arg Val Glu Cys Thr Thr Ile
2390                2395                2400

Val Asn Gly Met Lys Arg Ser Phe Tyr Val Tyr Ala Asn Gly Gly
2405                2410                2415

Arg Gly Phe Cys Lys Thr His Asn Trp Asn Cys Leu Asn Cys Asp
2420                2425                2430

Thr Phe Cys Thr Gly Ser Thr Phe Ile Ser Asp Glu Val Ala Arg
2435                2440                2445

Asp Leu Ser Leu Gln Phe Lys Arg Pro Ile Asn Pro Thr Asp Gln
2450                2455                2460

Ser Ser Tyr Ile Val Asp Ser Val Ala Val Lys Asn Gly Ala Leu
2465                2470                2475

His Leu Tyr Phe Asp Lys Ala Gly Gln Lys Thr Tyr Glu Arg His
2480                2485                2490

Pro Leu Ser His Phe Val Asn Leu Asp Asn Leu Arg Ala Asn Asn
2495                2500                2505

Thr Lys Gly Ser Leu Pro Ile Asn Val Ile Val Phe Asp Gly Lys
2510                2515                2520

Ser Lys Cys Asp Glu Ser Ala Ser Lys Ser Ala Ser Val Tyr Tyr
2525                2530                2535

Ser Gln Leu Met Cys Gln Pro Ile Leu Leu Leu Asp Gln Val Leu
2540                2545                2550

Val Ser Asp Val Gly Asp Ser Thr Glu Val Ser Val Lys Met Phe
2555                2560                2565

Asp Ala Tyr Val Asp Thr Phe Ser Ala Thr Phe Ser Val Pro Met
2570                2575                2580

Glu Lys Leu Lys Ala Leu Val Ala Thr Ala His Ser Glu Leu Ala
2585                2590                2595

Lys Gly Val Ala Leu Asp Gly Val Leu Ser Thr Phe Val Ser Ala
2600                2605                2610

Ala Arg Gln Gly Val Val Asp Thr Asp Val Asp Thr Lys Asp Val
2615                2620                2625

Ile Glu Cys Leu Lys Leu Ser His His Ser Asp Leu Glu Val Thr
2630                2635                2640

Gly Asp Ser Cys Asn Asn Phe Met Leu Thr Tyr Asn Lys Val Glu
2645                2650                2655

Asn Met Thr Pro Arg Asp Leu Gly Ala Cys Ile Asp Cys Asn Ala
2660                2665                2670

Arg His Ile Asn Ala Gln Val Ala Lys Ser His Asn Val Ser Leu
2675                2680                2685

Ile Trp Asn Val Lys Asp Tyr Met Ser Leu Ser Glu Gln Leu Arg
2690                2695                2700

Lys Gln Ile Arg Ser Ala Ala Lys Lys Asn Asn Ile Pro Phe Arg
2705                2710                2715

Leu Thr Cys Ala Thr Thr Arg Gln Val Val Asn Val Ile Thr Thr
2720                2725                2730

Lys Ile Ser Leu Lys Gly Gly Lys Ile Val Ser Thr Cys Phe Lys
2735                2740                2745

Leu Met Leu Lys Ala Thr Leu Leu Cys Val Leu Ala Ala Leu Val
2750                2755                2760
```

-continued

```
Cys Tyr Ile Val Met Pro Val His Thr Leu Ser Ile His Asp Gly
    2765                2770                2775

Tyr Thr Asn Glu Ile Ile Gly Tyr Lys Ala Ile Gln Asp Gly Val
    2780                2785                2790

Thr Arg Asp Ile Ile Ser Thr Asp Asp Cys Phe Ala Asn Lys His
    2795                2800                2805

Ala Gly Phe Asp Ala Trp Phe Ser Gln Arg Gly Gly Ser Tyr Lys
    2810                2815                2820

Asn Asp Lys Ser Cys Pro Val Val Ala Ala Ile Ile Thr Arg Glu
    2825                2830                2835

Ile Gly Phe Ile Val Pro Gly Leu Pro Gly Thr Val Leu Arg Ala
    2840                2845                2850

Ile Asn Gly Asp Phe Leu His Phe Leu Pro Arg Val Phe Ser Ala
    2855                2860                2865

Val Gly Asn Ile Cys Tyr Thr Pro Ser Lys Leu Ile Glu Tyr Ser
    2870                2875                2880

Asp Phe Ala Thr Ser Ala Cys Val Leu Ala Ala Glu Cys Thr Ile
    2885                2890                2895

Phe Lys Asp Ala Met Gly Lys Pro Val Pro Tyr Cys Tyr Asp Thr
    2900                2905                2910

Asn Leu Leu Glu Gly Ser Ile Ser Tyr Ser Glu Leu Arg Pro Asp
    2915                2920                2925

Thr Arg Tyr Val Leu Met Asp Gly Ser Ile Ile Gln Phe Pro Asn
    2930                2935                2940

Thr Tyr Leu Glu Gly Ser Val Arg Val Val Thr Thr Phe Asp Ala
    2945                2950                2955

Glu Tyr Cys Arg His Gly Thr Cys Glu Arg Ser Glu Val Gly Ile
    2960                2965                2970

Cys Leu Ser Thr Ser Gly Arg Trp Val Leu Asn Asn Glu His Tyr
    2975                2980                2985

Arg Ala Leu Ser Gly Val Phe Cys Gly Val Asp Ala Met Asn Leu
    2990                2995                3000

Ile Ala Asn Ile Phe Thr Pro Leu Val Gln Pro Val Gly Ala Leu
    3005                3010                3015

Asp Val Ser Ala Ser Val Val Ala Gly Gly Ile Ile Ala Ile Leu
    3020                3025                3030

Val Thr Cys Ala Ala Tyr Tyr Phe Met Lys Phe Arg Arg Val Phe
    3035                3040                3045

Gly Glu Tyr Asn His Val Val Ala Ala Asn Ala Leu Leu Phe Leu
    3050                3055                3060

Met Ser Phe Thr Ile Leu Cys Leu Val Pro Ala Tyr Ser Phe Leu
    3065                3070                3075

Pro Gly Val Tyr Ser Val Phe Tyr Leu Tyr Leu Thr Phe Tyr Phe
    3080                3085                3090

Thr Asn Asp Val Ser Phe Leu Ala His Leu Gln Trp Phe Ala Met
    3095                3100                3105

Phe Ser Pro Ile Val Pro Phe Trp Ile Thr Ala Ile Tyr Val Phe
    3110                3115                3120

Cys Ile Ser Leu Lys His Cys His Trp Phe Phe Asn Asn Tyr Leu
    3125                3130                3135

Arg Lys Arg Val Met Phe Asn Gly Val Thr Phe Ser Thr Phe Glu
    3140                3145                3150

Glu Ala Ala Leu Cys Thr Phe Leu Leu Asn Lys Glu Met Tyr Leu
```

-continued

Lys Leu Arg Ser Glu Thr Leu Leu Pro Leu Thr Gln Tyr Asn Arg
3155            3160            3165
                3170            3175            3180

Tyr Leu Ala Leu Tyr Asn Lys Tyr Lys Tyr Phe Ser Gly Ala Leu
3185            3190            3195

Asp Thr Thr Ser Tyr Arg Glu Ala Ala Cys Cys His Leu Ala Lys
3200            3205            3210

Ala Leu Asn Asp Phe Ser Asn Ser Gly Ala Asp Val Leu Tyr Gln
3215            3220            3225

Pro Pro Gln Thr Ser Ile Thr Ser Ala Val Leu Gln Ser Gly Phe
3230            3235            3240

Arg Lys Met Ala Phe Pro Ser Gly Lys Val Glu Gly Cys Met Val
3245            3250            3255

Gln Val Thr Cys Gly Thr Thr Thr Leu Asn Gly Leu Trp Leu Asp
3260            3265            3270

Asp Thr Val Tyr Cys Pro Arg His Val Ile Cys Thr Ala Glu Asp
3275            3280            3285

Met Leu Asn Pro Asn Tyr Glu Asp Leu Leu Ile Arg Lys Ser Asn
3290            3295            3300

His Ser Phe Leu Val Gln Ala Gly Asn Val Gln Leu Arg Val Ile
3305            3310            3315

Gly His Ser Met Gln Asn Cys Leu Leu Arg Leu Lys Val Asp Thr
3320            3325            3330

Ser Asn Pro Lys Thr Pro Lys Tyr Lys Phe Val Arg Ile Gln Pro
3335            3340            3345

Gly Gln Thr Phe Ser Val Leu Ala Cys Tyr Asn Gly Ser Pro Ser
3350            3355            3360

Gly Val Tyr Gln Cys Ala Met Arg Pro Asn His Thr Ile Lys Gly
3365            3370            3375

Ser Phe Leu Asn Gly Ser Cys Gly Ser Val Gly Phe Asn Ile Asp
3380            3385            3390

Tyr Asp Cys Val Ser Phe Cys Tyr Met His His Met Glu Leu Pro
3395            3400            3405

Thr Gly Val His Ala Gly Thr Asp Leu Glu Gly Lys Phe Tyr Gly
3410            3415            3420

Pro Phe Val Asp Arg Gln Thr Ala Gln Ala Ala Gly Thr Asp Thr
3425            3430            3435

Thr Ile Thr Leu Asn Val Leu Ala Trp Leu Tyr Ala Ala Val Ile
3440            3445            3450

Asn Gly Asp Arg Trp Phe Leu Asn Arg Phe Thr Thr Thr Leu Asn
3455            3460            3465

Asp Phe Asn Leu Val Ala Met Lys Tyr Asn Tyr Glu Pro Leu Thr
3470            3475            3480

Gln Asp His Val Asp Ile Leu Gly Pro Leu Ser Ala Gln Thr Gly
3485            3490            3495

Ile Ala Val Leu Asp Met Cys Ala Ala Leu Lys Glu Leu Leu Gln
3500            3505            3510

Asn Gly Met Asn Gly Arg Thr Ile Leu Gly Ser Thr Ile Leu Glu
3515            3520            3525

Asp Glu Phe Thr Pro Phe Asp Val Val Arg Gln Cys Ser Gly Val
3530            3535            3540

Thr Phe Gln Gly Lys Phe Lys Lys Ile Val Lys Gly Thr His His
3545            3550            3555

-continued

Trp Met Leu Leu Thr Phe Leu Thr Ser Leu Leu Ile Leu Val Gln
3560            3565            3570

Ser Thr Gln Trp Ser Leu Phe Phe Val Tyr Glu Asn Ala Phe
3575            3580            3585

Leu Pro Phe Thr Leu Gly Ile Met Ala Ile Ala Ala Cys Ala Met
3590            3595            3600

Leu Leu Val Lys His Lys His Ala Phe Leu Cys Leu Phe Leu Leu
3605            3610            3615

Pro Ser Leu Ala Thr Val Ala Tyr Phe Asn Met Val Tyr Met Pro
3620            3625            3630

Ala Ser Trp Val Met Arg Ile Met Thr Trp Leu Glu Leu Ala Asp
3635            3640            3645

Thr Ser Leu Ser Gly Tyr Arg Leu Lys Asp Cys Val Met Tyr Ala
3650            3655            3660

Ser Ala Leu Val Leu Leu Ile Leu Met Thr Ala Arg Thr Val Tyr
3665            3670            3675

Asp Asp Ala Ala Arg Arg Val Trp Thr Leu Met Asn Val Ile Thr
3680            3685            3690

Leu Val Tyr Lys Val Tyr Tyr Gly Asn Ala Leu Asp Gln Ala Ile
3695            3700            3705

Ser Met Trp Ala Leu Val Ile Ser Val Thr Ser Asn Tyr Ser Gly
3710            3715            3720

Val Val Thr Thr Ile Met Phe Leu Ala Arg Ala Ile Val Phe Val
3725            3730            3735

Cys Val Glu Tyr Tyr Pro Leu Leu Phe Ile Thr Gly Asn Thr Leu
3740            3745            3750

Gln Cys Ile Met Leu Val Tyr Cys Phe Leu Gly Tyr Cys Cys Cys
3755            3760            3765

Cys Tyr Phe Gly Leu Phe Cys Leu Leu Asn Arg Tyr Phe Arg Leu
3770            3775            3780

Thr Leu Gly Val Tyr Asp Tyr Leu Val Ser Thr Gln Glu Phe Arg
3785            3790            3795

Tyr Met Asn Ser Gln Gly Leu Leu Pro Pro Lys Ser Ser Ile Asp
3800            3805            3810

Ala Phe Lys Leu Asn Ile Lys Leu Leu Gly Ile Gly Gly Lys Pro
3815            3820            3825

Cys Ile Lys Val Ala Thr Val Gln Ser Lys Met Ser Asp Val Lys
3830            3835            3840

Cys Thr Ser Val Val Leu Leu Ser Val Leu Gln Gln Leu Arg Val
3845            3850            3855

Glu Ser Ser Ser Lys Leu Trp Ala Gln Cys Val Gln Leu His Asn
3860            3865            3870

Asp Ile Leu Leu Ala Lys Asp Thr Thr Glu Ala Phe Glu Lys Met
3875            3880            3885

Val Ser Leu Leu Ser Val Leu Leu Ser Met Gln Gly Ala Val Asp
3890            3895            3900

Ile Asn Arg Leu Cys Glu Glu Met Leu Asp Asn Arg Ala Thr Leu
3905            3910            3915

Gln Ala Ile Ala Ser Glu Phe Ser Ser Leu Pro Ser Tyr Ala Ala
3920            3925            3930

Tyr Ala Thr Ala Gln Glu Ala Tyr Glu Gln Ala Val Ala Asn Gly
3935            3940            3945

```
Asp Ser Glu Val Val Leu Lys Lys Leu Lys Lys Ser Leu Asn Val
    3950                3955                3960

Ala Lys Ser Glu Phe Asp Arg Asp Ala Met Gln Arg Lys Leu
    3965                3970                3975

Glu Lys Met Ala Asp Gln Ala Met Thr Gln Met Tyr Lys Gln Ala
    3980                3985                3990

Arg Ser Glu Asp Lys Arg Ala Lys Val Thr Ser Ala Met Gln Thr
    3995                4000                4005

Met Leu Phe Thr Met Leu Arg Lys Leu Asp Asn Asp Ala Leu Asn
    4010                4015                4020

Asn Ile Ile Asn Asn Ala Arg Asp Gly Cys Val Pro Leu Asn Ile
    4025                4030                4035

Ile Pro Leu Thr Thr Ala Ala Lys Leu Met Val Val Val Pro Asp
    4040                4045                4050

Tyr Gly Thr Tyr Lys Asn Thr Cys Asp Gly Asn Thr Phe Thr Tyr
    4055                4060                4065

Ala Ser Ala Leu Trp Glu Ile Gln Gln Val Val Asp Ala Asp Ser
    4070                4075                4080

Lys Ile Val Gln Leu Ser Glu Ile Asn Met Asp Asn Ser Pro Asn
    4085                4090                4095

Leu Ala Trp Pro Leu Ile Val Thr Ala Leu Arg Ala Asn Ser Ala
    4100                4105                4110

Val Lys Leu Gln Asn Asn Glu Leu Ser Pro Val Ala Leu Arg Gln
    4115                4120                4125

Met Ser Cys Ala Ala Gly Thr Thr Gln Thr Ala Cys Thr Asp Asp
    4130                4135                4140

Asn Ala Leu Ala Tyr Tyr Asn Asn Ser Lys Gly Gly Arg Phe Val
    4145                4150                4155

Leu Ala Leu Leu Ser Asp His Gln Asp Leu Lys Trp Ala Arg Phe
    4160                4165                4170

Pro Lys Ser Asp Gly Thr Gly Thr Ile Tyr Thr Glu Leu Glu Pro
    4175                4180                4185

Pro Cys Arg Phe Val Thr Asp Thr Pro Lys Gly Pro Lys Val Lys
    4190                4195                4200

Tyr Leu Tyr Phe Ile Lys Gly Leu Asn Asn Leu Asn Arg Gly Met
    4205                4210                4215

Val Leu Gly Ser Leu Ala Ala Thr Val Arg Leu Gln Ala Gly Asn
    4220                4225                4230

Ala Thr Glu Val Pro Ala Asn Ser Thr Val Leu Ser Phe Cys Ala
    4235                4240                4245

Phe Ala Val Asp Pro Ala Lys Ala Tyr Lys Asp Tyr Leu Ala Ser
    4250                4255                4260

Gly Gly Gln Pro Ile Thr Asn Cys Val Lys Met Leu Cys Thr His
    4265                4270                4275

Thr Gly Thr Gly Gln Ala Ile Thr Val Thr Pro Glu Ala Asn Met
    4280                4285                4290

Asp Gln Glu Ser Phe Gly Gly Ala Ser Cys Cys Leu Tyr Cys Arg
    4295                4300                4305

Cys His Ile Asp His Pro Asn Pro Lys Gly Phe Cys Asp Leu Lys
    4310                4315                4320

Gly Lys Tyr Val Gln Ile Pro Thr Thr Cys Ala Asn Asp Pro Val
    4325                4330                4335

Gly Phe Thr Leu Arg Asn Thr Val Cys Thr Val Cys Gly Met Trp
```

-continued

```
                4340                4345                4350
Lys Gly Tyr Gly Cys Ser Cys Asp Gln Leu Arg Glu Pro Leu Met
            4355                4360                4365
Gln Ser Ala Asp Ala Ser Thr Phe Leu Asn Gly Phe Ala Val
        4370                4375                4380

<210> SEQ ID NO 32
<211> LENGTH: 13
<212> TYPE: PRT
<213> ORGANISM: Artificial
<220> FEATURE:
<223> OTHER INFORMATION: HBV core 128

<400> SEQUENCE: 32

Thr Pro Pro Ala Tyr Arg Pro Pro Asn Ala Pro Ile Leu
1               5                   10

<210> SEQ ID NO 33
<211> LENGTH: 19
<212> TYPE: DNA
<213> ORGANISM: Artificial
<220> FEATURE:
<223> OTHER INFORMATION: CpG5002

<400> SEQUENCE: 33
tccatgacgt tctgatgtt                                              19

<210> SEQ ID NO 34
<211> LENGTH: 9
<212> TYPE: PRT
<213> ORGANISM: SARS coronavirus

<400> SEQUENCE: 34

Phe Ile Ala Gly Leu Ile Ala Ile Val
1               5
```